US012722305B2

(12) United States Patent
Tani et al.

(10) Patent No.: US 12,722,305 B2
(45) Date of Patent: Sep. 1, 2026

(54) ROBOTIC SURGICAL SYSTEM, OPERATION APPARATUS AND ROBOTIC-SURGICAL-SYSTEM CONTROL METHOD

(71) Applicant: KAWASAKI JUKOGYO KABUSHIKI KAISHA, Kobe (JP)

(72) Inventors: Hidenori Tani, Kobe (JP); Daisuke Yamamoto, Kobe (JP); Kazuki Kodama, Kobe (JP); Takeshi Kurihara, Kobe (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 74 days.

(21) Appl. No.: 18/645,614

(22) Filed: Apr. 25, 2024

(65) Prior Publication Data

US 2024/0359334 A1 Oct. 31, 2024

(30) Foreign Application Priority Data

Apr. 26, 2023 (JP) ................................ 2023-072614

(51) Int. Cl.

| | |
|---|---|
| ***A61B 34/00*** | (2016.01) |
| ***A61B 34/37*** | (2016.01) |
| ***B25J 9/16*** | (2006.01) |
| ***B25J 13/06*** | (2006.01) |

(52) U.S. Cl.

CPC ............... *B25J 13/06* (2013.01); *A61B 34/37* (2016.02); *A61B 34/77* (2016.02); *B25J 9/1633* (2013.01)

(58) Field of Classification Search

CPC ......... B25J 13/06; B25J 9/1633; A61B 34/37; A61B 34/77; A61B 34/74; A61B 2090/064; A61B 34/76; A61B 2017/00199; A61B 2017/00225; A61B 2034/254; A61B 2090/508

See application file for complete search history.

(56) References Cited

U.S. PATENT DOCUMENTS

| | | | |
|---|---|---|---|
| 6,994,703 B2 | 2/2006 | Wang et al. | |
| 9,423,869 B2 | 8/2016 | Yanagihara | |
| 11,027,430 B2 * | 6/2021 | Thackston | B25J 9/1689 |
| 11,305,422 B2 * | 4/2022 | Kasai | B25J 13/088 |
| 12,575,899 B2 * | 3/2026 | Romo | A61B 34/30 |
| 2004/0243110 A1 | 12/2004 | Niemeyer | |
| 2006/0106493 A1 | 5/2006 | Niemeyer et al. | |
| 2015/0018841 A1 * | 1/2015 | Seo | A61B 34/77 606/130 |
| 2017/0042730 A1 * | 2/2017 | He | A61B 34/30 |
| 2022/0370165 A1 * | 11/2022 | Cuthbertson | G05G 9/047 |
| 2022/0387120 A1 * | 12/2022 | Tanabe | A61B 34/37 |
| 2023/0034631 A1 | 2/2023 | Takano et al. | |

FOREIGN PATENT DOCUMENTS

| | | |
|---|---|---|
| EP | 2332484 B2 | 6/2022 |
| EP | 4140437 A1 | 3/2023 |
| JP | 2022-187879 A | 12/2022 |
| JP | 2023-20582 A | 2/2023 |

* cited by examiner

*Primary Examiner* — Robert T Nguyen
(74) *Attorney, Agent, or Firm* — METROLEX IP LAW GROUP, PLLC; Robert L. Scott, Esq.

(57) ABSTRACT

A robotic surgical system according to this disclosure includes a controller configured to control a driver(s) to apply a force in a direction opposite to a direction of operation of an operation unit in a three-axis Cartesian coordinate system having three axes orthogonal to each other.

17 Claims, 17 Drawing Sheets

500
30
32 33
100
40
20
32
33
50
32
50a
50b
31
60
10
50d
1
2
50c
33
3
1
310
320
330
P
200
150
140
220
141
160
161
400
110L
210
130
240
300
230
110
110R
120
340

500
400
IMAGE PRO-CESSING UNIT
351
STORAGE
350
2nd CONTROLLER
220
DISPLAY
10
VISION UNIT
300
22
INPUT
310
1st CONT-ROLLER
311
STORAGE
OPERATION CONT-ROLLER
OPERATION CONT-ROLLER
340
340
POSITIONER CONTROLLER
330
ARM CONTROLLER
320
SC
SM
EN
110L
110R
110
200
30
40
360
60
ARM OPERA-TION UNIT
50
41
STATUS INDICATOR
42
ARM STATUS INDICATOR
23
OPERATION HANDLE
23a
THROTTLE GRIP
22b
JOYSTICK
24
STABILIZER
25
ELECTRIC CYLINDER

OPERATION PARAMETER PA

TH1

0

OPERATION VELOCITY V (ABSOLUTE VALUE)

$-\alpha 1$ $-\beta 1$ $-\gamma 1$ $-\delta 1$

IN DECELERATION 110

IN ACCELERATION 110

ROBOTIC SURGICAL SYSTEM, OPERATION APPARATUS AND ROBOTIC-SURGICAL-SYSTEM CONTROL METHOD

CROSS-REFERENCE TO RELATED APPLICATION

The priority application number JP2023-072614, Robotic Surgical System, Operation Apparatus and Robotic-Surgical-System Control Method, Apr. 26, 2023, TANI Hidenori, YAMAMOTO Daisuke, KODAMA Kazuki, and KURIHARA Takeshi, upon which this patent application is based, are hereby incorporated by reference.

BACKGROUND OF THE INVENTION

Field of the Invention

The present disclosure relates to a robotic surgical system, an operation apparatus and a robotic-surgical-system control method.

Description of the Background Art

Robotic surgical systems are is known in the art. For example, United States patent application publication No. US2004/0243110 discloses a robotic surgical system including a master controller including an operation unit configured to accept an operation from an operator, and a multi-joint robot arm as a slave configured to support a medical instrument and to be controlled in accordance with an amount of the operation accepted by the operation unit.

The operation unit of the master controller in United States patent application publication No. US2004/0243110 is constructed of multi-joint arm including a plurality of links. The multi-joint arm is suspended with being formed in an L shape. Also, the multi-joint arm includes electric motors. Accordingly, the multi-joint arm can be kept in the L shape by generating motor torques against gravity without being manually supported by the operator.

The electric motors generate forces in accordance with an operation velocity of the operation unit operated by the operator to compensate for friction forces of gears connected between the electric motors and the master controller in United States patent application publication No. US2004/0243110. Accordingly, the user can feel light when operating the operation unit.

However, in a case in which the electric motors generate forces to make user feel light when operating the operation unit as in United States patent application publication No. US2004/0243110, the operation unit is likely to sway due to the light operation feeling of the operation unit when the user linearly operates the operation unit. For this reason, it is desired to improve stability of operation of the operation unit when users linearly operate the operation unit.

SUMMARY OF THE INVENTION

The present disclosure provides a robotic surgical system, an operation apparatus and a robotic-surgical-system control method capable of improving stability of operation of an operation unit when being linearly operated.

A robotic surgical system according to a first aspect of the present disclosure includes a surgical apparatus including a robot arm configured to support a medical instrument; an operation apparatus including an operation unit that is configured to accept operation of an operator and includes a driver(s) configured to assist the operation of the operator, and being configured to operate the surgical apparatus; and a controller configured to control the driver(s) to apply a force in a direction opposite to a direction of the operation of the operation unit in a three-axis Cartesian coordinate system having three axes orthogonal to each other.

In the robotic surgical system according to the first aspect of the present disclosure, the controller configured to control the driver(s) to apply a force in a direction opposite to a direction of the operation of the operation unit in a three-axis Cartesian coordinate system having three axes orthogonal to each other is provided. Accordingly, because operation feeling of the operation unit can be heavy, it is possible to prevent the operation unit from swaying due to light operation feeling of the operation unit when users linearly operate the operation unit. Consequently, it is possible to improve stability of operation of the operation unit when users linearly operate the operation unit.

An operation apparatus for operating a surgical apparatus including a robot arm configured to support a medical instrument according to a second aspect of the present disclosure includes an operation unit that is configured to accept operation of an operator and includes a driver(s) configured to assist the operation of the operator; and a controller configured to control the driver(s) to apply a force in a direction opposite to a direction of the operation of the operation unit in a three-axis Cartesian coordinate system having three axes orthogonal to each other.

In the operation apparatus according to the second aspect of the present disclosure, the controller configured to control the driver(s) to apply a force in a direction opposite to a direction of the operation of the operation unit in a three-axis Cartesian coordinate system having three axes orthogonal to each other is provided. Accordingly, because operation feeling of the operation unit can be heavy, it is possible to prevent the operation unit from swaying due to light operation feeling of the operation unit when users linearly operate the operation unit. Consequently, it is possible to provide an operation apparatus capable of improving stability of operation of the operation unit when users linearly operate the operation unit.

A robotic-surgical-system control method according to a third aspect of the present disclosure is a method for controlling a robotic surgical system including a surgical apparatus including a robot arm configured to support a medical instrument, and an operation apparatus including an operation unit that is configured to accept operation of an operator and includes a driver(s) configured to assist the operation of the operator, and being configured to operate the surgical apparatus, the method including accepting the operation of the operation unit; and controlling the driver(s) to apply a force in a direction opposite to a direction of the operation of the operation unit in a three-axis Cartesian coordinate system having three axes orthogonal to each other.

In the robotic-surgical-system control method according to the third aspect of the present disclosure, as discussed above, controlling the driver(s) to apply a force in a direction opposite to a direction of the operation of the operation unit in a three-axis Cartesian coordinate system having three axes orthogonal to each other is provided. Accordingly, because operation feeling of the operation unit can be heavy, it is possible to prevent the operation unit from swaying due to light operation feeling of the operation unit when users linearly operate the operation unit. Consequently, it is possible to provide a robotic-surgical-system control method capable of improving stability of operation of the operation unit when users linearly operate the operation unit.

According to this disclosure, it is possible to improve stability of operation of the operation unit when users linearly operate the operation unit.

Figure 1:
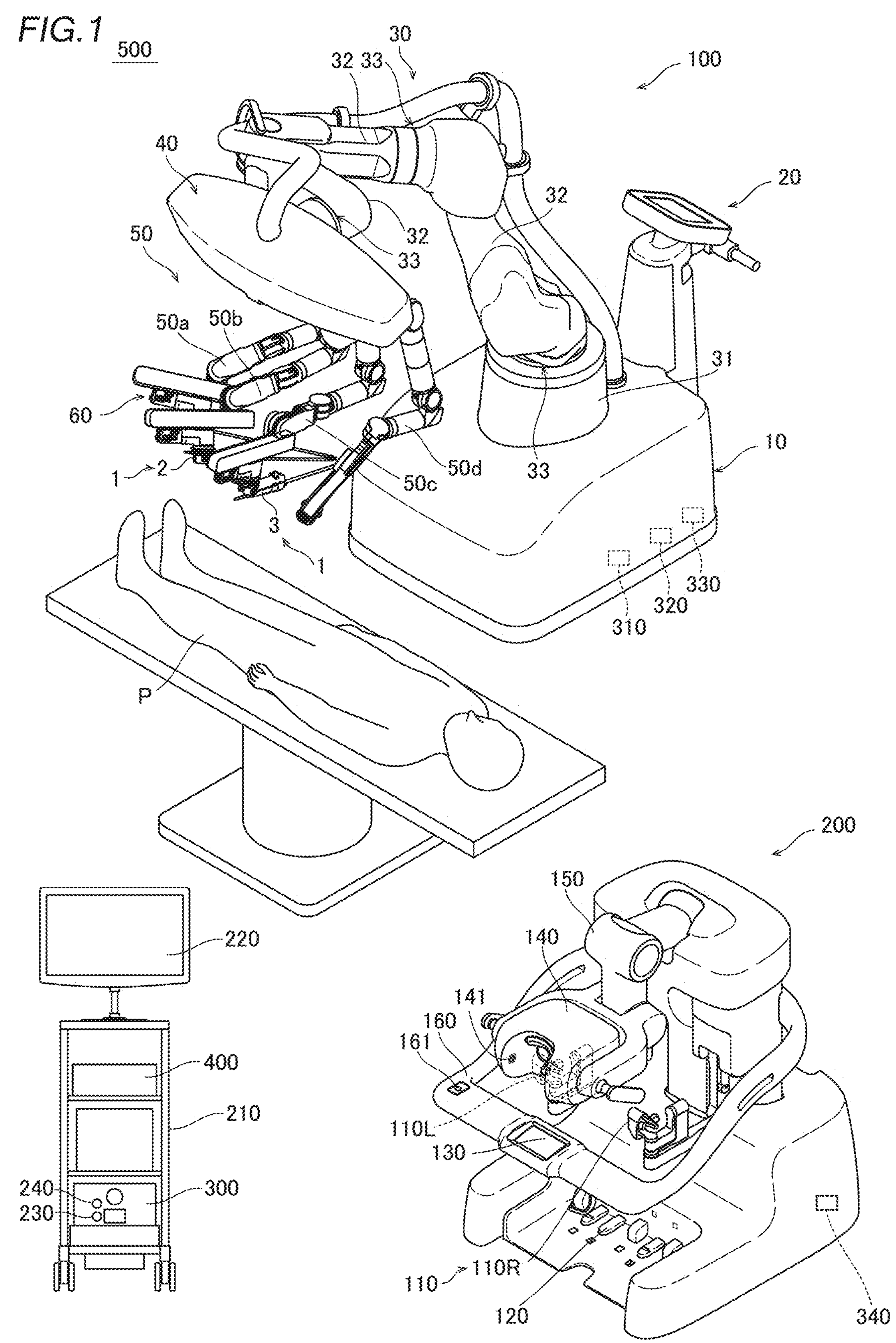
FIG. 1 is a block diagram showing a configuration of a robotic surgical system according to one embodiment.

DESCRIPTION OF THE PREFERRED EMBODIMENT (Configuration of Robotic Surgical System)

The structure of the robotic surgical system 500 by this embodiment is explained. The robotic surgical system 500 includes a surgical robot 100, a remote control apparatus 200, a vision unit 300 and an image processing unit 400. The surgical robot 100 and the remote control apparatus 200 are an example of a surgical apparatus and an example of an operation device, respectively.

Figure 4:
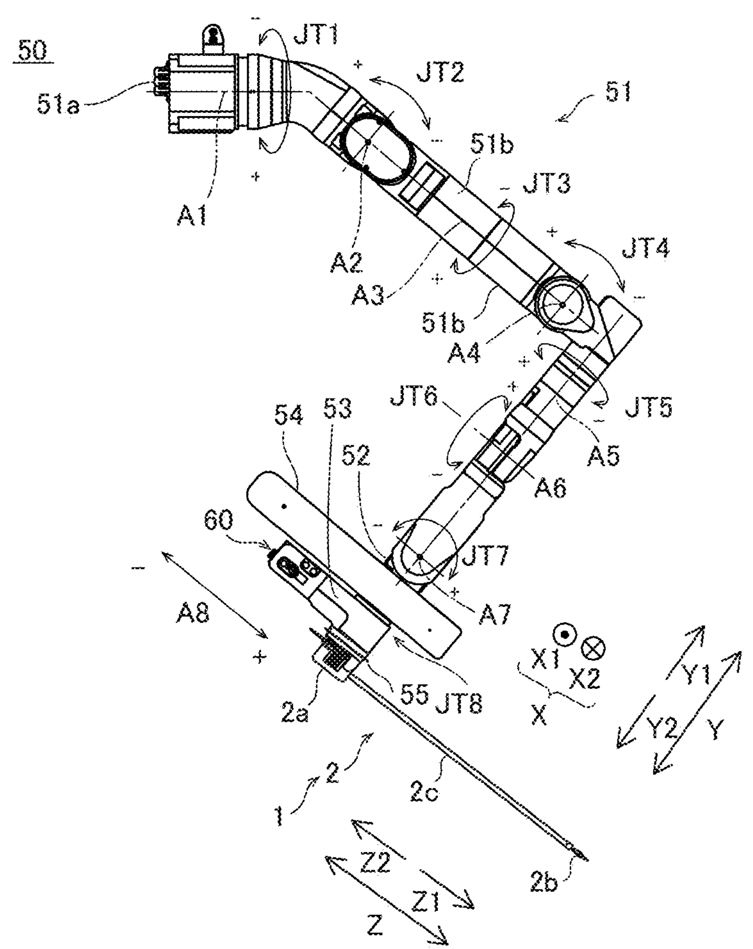
FIG. 4 is a block diagram showing a configuration of a robot arm according to the one embodiment.

In this specification, a longitudinal direction of a surgical instrument 1 is defined as a Z direction as shown in FIG. 4. A distal part of the surgical instrument 1 is defined as a z1 side, and a proximal part of the surgical instrument 1 is defined as a Z2 side. A direction orthogonal to the Z direction is defined as an X direction. One side in the X direction is defined as an X1 side, and another side is defined as an X2 side. A direction orthogonal to the Z direction and the X direction is defined as a Y direction. One side in the Y direction is defined as an Y1 side, and another side is defined as an Y2 side.

Figure 3:
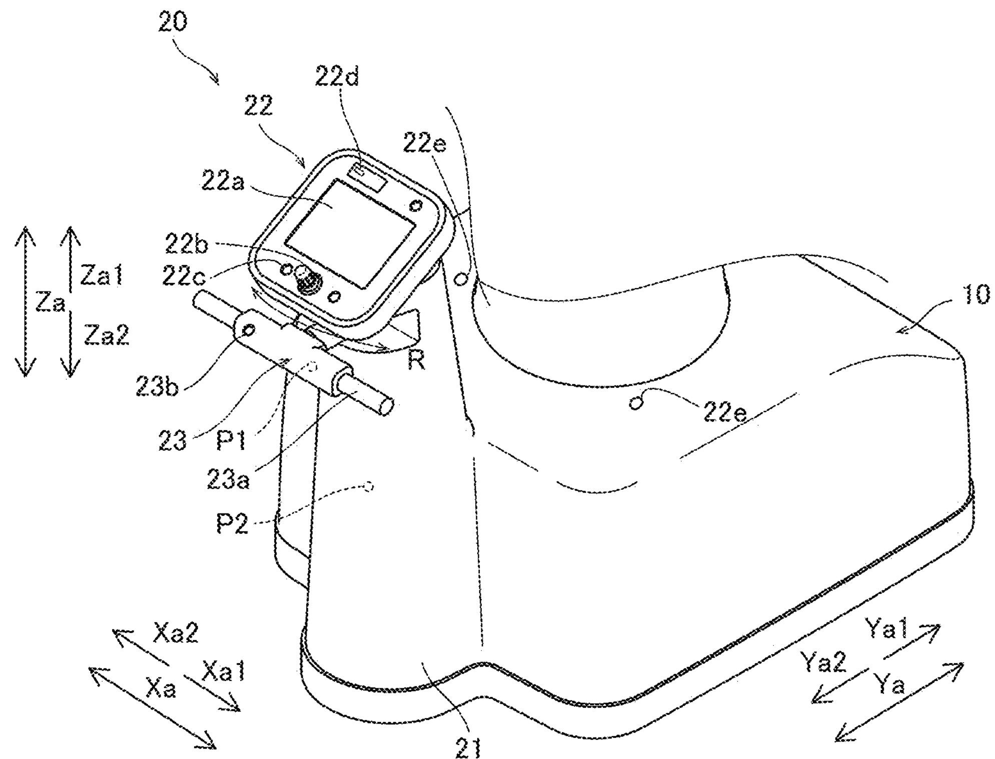
FIG. 3 is a diagram showing a configuration of the medical cart according to the one embodiment.

In this specification, a leftward/rightward direction from the viewpoint of an operator who operates a display **22*a* of an input 22 is defined as an Xa direction as shown in FIG. 3. A rightward direction is defined as an Xa1 direction, and a leftward direction is defined as an Xa2 direction. A frontward/rearward direction from the viewpoint of the operator who operates the display 22*a* of the input 22 is defined as a Ya direction. A frontward direction is defined as an Ya1 direction, and a rearward direction is defined as an Ya2 direction. A direction orthogonal to a floor on which the surgical robot 100** is arranged is defined as a Za direction. An upward direction is defined as a Za1 direction, and a downward direction is defined as a Za2 direction.

In this specification, a direction orthogonal to a floor on which the remote control apparatus 200 is placed is defined as a Zb direction, the frontward/rearward direction of the operator who operates the operation unit 110, which is orthogonal to the Zb direction, is defined a Yb direction, and a direction orthogonal to the Zb direction and the Yb direction is defined as an Xb direction. In the Zb directions, an upward direction is defined as a Zb1 direction, and a downward direction is defined as a Zb2 direction. In the Yb directions, one is defined as an Yb1 direction, and another is defined as an Yb2 direction. In the Xb directions, one is defined as an Xb1 direction, and another is defined as an Xb2 direction.

As shown in FIG. 1, the surgical robot 100 is arranged in an operating room. The remote control apparatus 200 is located remote from the surgical robot 100. Also, the remote control apparatus 200 is configured to receive instructions as to the surgical instruments 1. Specifically, an operator, such as a doctor, can provide the remote control apparatus 200 with an instruction to instruct a desired motion of the surgical robot 100. The remote control apparatus 200 transmits the provided command to the surgical robot 100. The surgical robot 100 is configured to perform the motion in accordance with the command received. The surgical robot 100 is arranged in the operating room, which is a sterile field.

(Configuration of Surgical Robot)

As shown in FIG. 1, the surgical robot 100 includes a medical cart 10, a cart positioner operation unit 20, a positioner 30, an arm base 40, a plurality of robot arms 50 and arm operation units 60 provided in the robot arms 50.

As shown in FIG. 3, the cart positioner operation unit 20 is arranged in a rear part of the medical cart 10 and supported by a cart positioner operation support 21, and the medical cart 10 or the positioner 30 can be moved in accordance with a manual operation of the cart positioner operation unit 20. The cart positioner operation unit 20 includes the input 22 and an operating handle 23. The input 22 is configured to accept instructions to move or change orientations of the positioner 30, the arm base 40 and the plurality of robot arms 50 to prepare a surgical operation mainly before the operation is carried out. The cart positioner operation unit 20 includes the operating handle 23, a stabilizer 24 and an electric cylinder 25 shown in FIG. 15.

Figure 2:
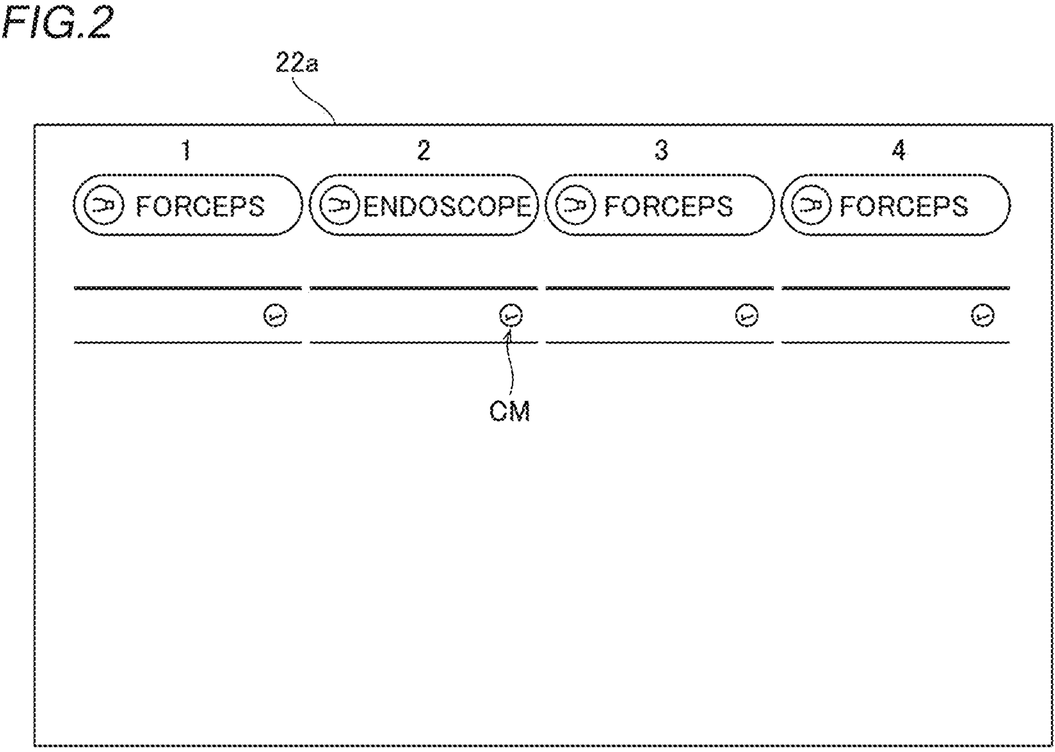
FIG. 2 is a diagram showing a display of a medical cart according to the one embodiment.

As shown in FIG. 3, the input 22 of the cart positioner operation unit 20 includes the display 22*a*, a joystick 22*b*, an enable switch 22*c*, an error reset button 22*d* and speakers 22*e*. For example, the display 22*a* is a liquid crystal panel. As shown in FIG. 2, the display 22*a* indicates numbers corresponding to the plurality of robot arms 50. Also, the display 22*a* indicates types of surgical instruments 1 attached to the plurality of robot arms 50. The display 22*a* indicates checkmarks CM representing that their pivot positions PP (discussed later) have been set.

As shown in FIG. 3, the joystick 22*b* is arranged in proximity to the display 22*a* of the input 22 of the cart positioner operation unit 20. When an operation mode displayed on the display 22*a* is selected, the positioner 30 can be three-dimensionally moved by operating the joystick 22*b*.

The enable switch 22*c* is arranged in proximity to the joystick 22*b* of the cart positioner operation unit 20. The enable switch 22*c* is configured to enable or disable movement of the positioner 30. When the enable switch 22*c* is pressed so that movement of the positioner 30 is enabled, the positioner 30 can be moved in accordance with a manual operation of the joystick 22*b*.

The error reset button 22*d* is configured to reset an error of the robotic surgical system 500. An exemplary error is an error of abnormal deviation. The speakers 22*e* are a pair of speakers. The pair of speakers 22*e* are arranged at a position in the medical cart 10 in proximity to the positioner 30.

Also, the operating handle 23 is arranged in proximity to the display 22*a* of the cart positioner operation unit 20. The operating handle 23 includes a throttle grip 23*a* that is configured to be gripped and twisted by an operator such as nurse, engineer, etc. to control movement of the medical cart 10. Specifically, the operating handle 23 is arranged under the input 22. The medical cart 10 can move forward when the throttle grip 23*a* is twisted from a near side toward a far side. The medical cart 10 can move backward when the throttle grip 23*a* is twisted from the far side toward the near side. A speed of the medical cart 10 can be changed in accordance with a twisting amount of the throttle grip 23*a*. In addition, the operating handle 23 is configured to swing leftward and rightward as shown by an R direction, and to rotate the medical cart 10 depending on the swinging operation of the operating handle 23.

Also, the operating handle 23 of the cart positioner operation unit 20 includes an enable switch 23*b* configured to enable or disable movement of the medical cart 10. When the enable switch 23*b* is pressed so that movement of the medical cart 10 is enabled, the medical cart 10 can be moved in accordance with a manual operation of the throttle grip 23*a* of the operating handle 23.

For example, as shown in FIG. 1, the positioner 30 is constructed of a 7-axis multi-joint robot. The positioner 30 is arranged on the medical cart 10. The positioner 30 is configured to adjust a position of the arm base 40. The positioner 30 can three-dimensionally move the position of the arm base 40.

The positioner 30 includes a base 31, and a plurality of links 32 coupled to the base 31. The links 32 are coupled to each other by joints 33.

The arm base 40 is attached to a distal end of the positioner 30. In the plurality of robot arms 50, the proximal end of each robot arm 50 is attached to the arm base 40. The plurality of robot arms 50 are foldable into a storage posture. The arm base 40 and the plurality of robot arms 50 covered by sterile drapes when used. The robot arms 50 are configured to support surgical instruments 1.

Figure 15:
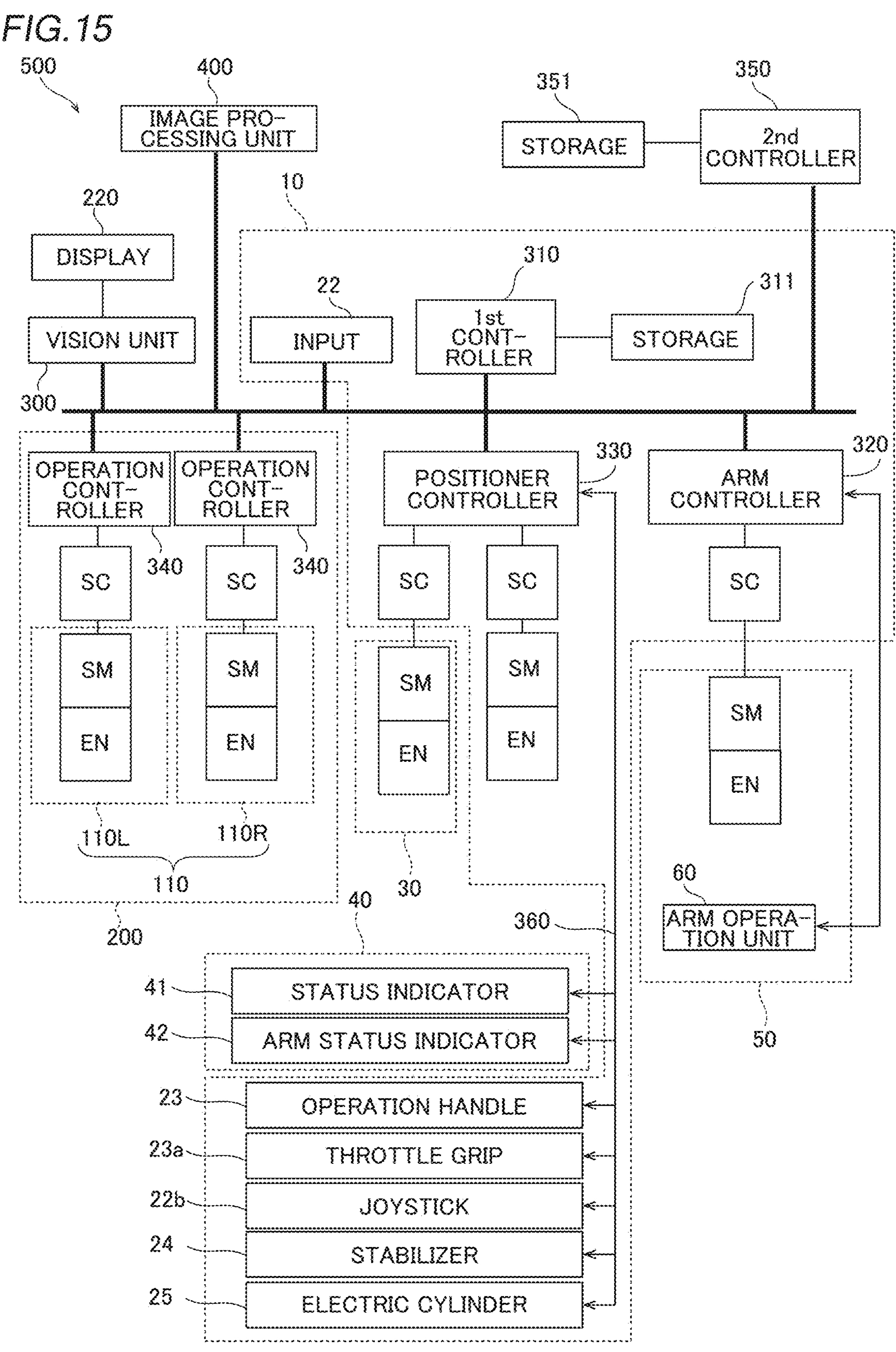
FIG. 15 is a control block diagram of a surgical robot according to the one embodiment.

A status indicator 41 and an arm status indicator 42 shown in FIG. 15 are provided in the arm base 40. The status indicator 41 is configured to indicate a status of robotic surgical system 500. The arm status indicator 42 is configured to indicate states of robot arms 50.

Two or more robot arms 50 are provided as a plurality of robot arms. Specifically, four robot arms 50*a*, 50*b*, 50*c* and 50*d* are provided. The robot arms 50*a*, 50*b*, 50*c* and 50*d* have a similar configuration to each other.

As shown in FIG. 4, each robot arm 50 includes an arm 51, a first link part 52, a second link part 53, and a translation mechanism 54. The robot arm 50 includes joints JT1, JT2, JT3, JT4, JT5, JT6, JT7 and JT8. The joints JT1, JT2, JT3, JT4, JT5, JT6 and JT7 have A1, A2, A3, A4, A5, A6 and A7 axes as their rotation axes. JT8 has an A8 axis as its linear-motion axis. The axes from A1 to A7 are rotation axes of the joints JT1 to JT7 of the arm 51. The A7 axis is a rotational axis of the first link part 52. The A8 axis is a linear-motion axis along which the second link part 53 is moved relative to the first link part 52 in the Z direction by the translation mechanism 54. The arm 51 includes a base 51*a* and a link part 51*b*.

The arm 51 is constructed of a 7-axis multi-joint robot arm. The first link part 52 is arranged in a distal end of arm 51. The arm operation unit 60 discussed later is attached to the second link part 53. The translation mechanism 54 is arranged between the first link part 52 and the second link part 53. The second link part 53 includes a holder 55 configured to hold the surgical instrument 1. The translation mechanism 54 is configured to translationally move the holder 55 to which the surgical instrument 1 is attached between a first position and a second position. The first position is a position of a Z2-direction side end of a moving range of the holder 55 moved by the translation mechanism 54 along the A8 axis. The second position is a position of a z1-direction side end of the moving range of the holder 55 moved by the translation mechanism 54 along the A8 axis.

Figure 9:
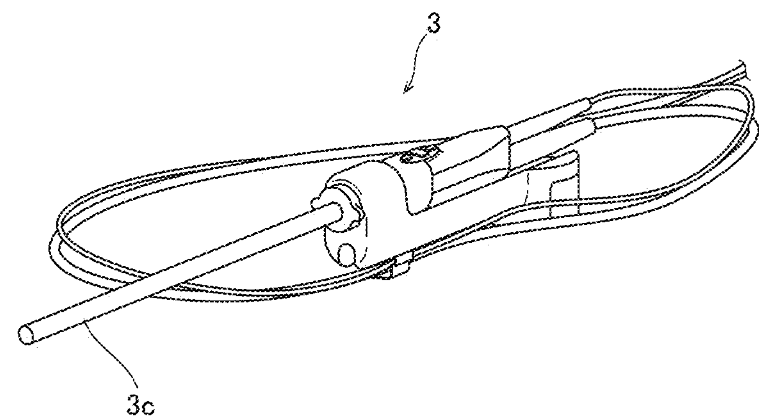
FIG. 9 is a diagram showing an endoscope.
Figure 10:
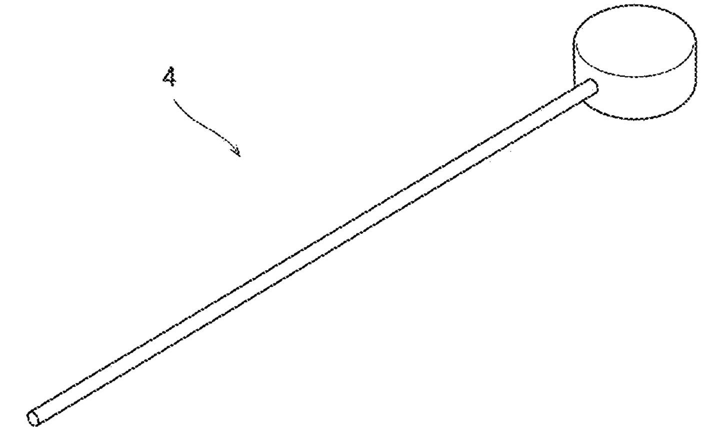
FIG. 10 is a diagram showing a pivot-position setting tool.

Each robot arm 50 is configured to support the surgical instrument 1. Surgical instruments 1 can be attached to the distal ends of the plurality of robot arms 50. The surgical instruments 1 include, for example, replaceable instruments 2, an endoscope 3 (see FIG. 9) configured to capture images of a part to be operated, a pivot-position setting tool 4 (see FIG. 10) to set a pivot position PP described below, etc. The instrument 2 includes a driven unit 2*a*, a forceps 2*b* and a shaft 2*c*. The surgical instrument 1 is an example of a medical instrument.

As shown in FIG. 1, an endoscope 3 is attached to the distal end of one, e.g., the robot arm 50*c* of the robot arms 50, and the instruments 2 are attached to the distal ends of the others, e.g., the robot arms 50*a*, 50*b* and 50*d*. The endoscope 3 is preferably attached to one of two robot arms 50*b* and 50*c*, which are located in a central part, of the four robot arms 50 arranged adjacent to each other.

(Configuration of Instrument)

Figure 5:
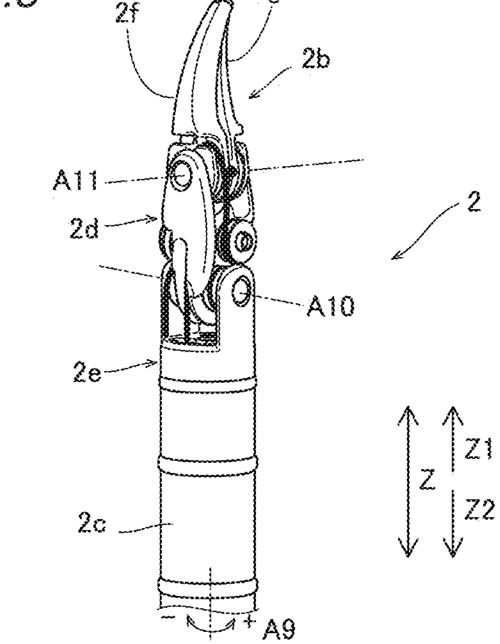
FIG. 5 is a diagram showing a forceps.

For example, as shown in FIG. 5, a forceps 2*b* is attached to the distal end of the instrument 2. Tools that include a joint and can be attached to the distal end of the instrument 2 can include scissors, a grasper, a needle holder, a microdissector, a staple applier, a tucker, a vacuum cleaning tool, a snare wire, a clip applier, etc., other than the forceps 2*b*. Tools that do not include any joint and can be attached to the distal end of the instrument 2 can include a cutting blade, a cautery probe, a cleaner, a catheter, a vacuum orifice, etc.

The forceps 2*b* includes a first support 2*d* and a second support 2*e*. The first support 2*d* is configured to rotatably support a base end side of jaws 2*f* and 2*g* about a A11 axis. The second support 2*e* is rotatably configured to support a base-end side of the first support 2*d* about a A10 axis. The shaft 2*c* can rotate about a A9 axis. The jaws 2*f* and 2*g* can rotate about the A11 axis to open and close.

(Configuration of Arm Operation Unit)

Figure 6:
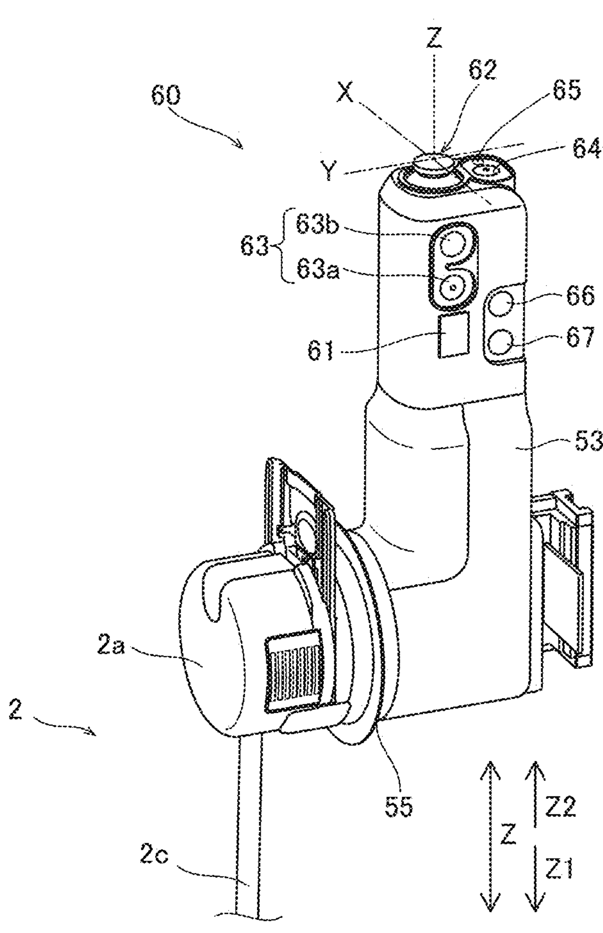
FIG. 6 is a block diagram showing a configuration of an arm operation unit according to the one embodiment.

As shown in FIG. 6, the arm operation unit 60 is mounted to the robot arm 50, and is configured to operate the robot arm 50. Specifically, the arm operation unit 60 is mounted to the second link part 53.

The arm operation unit 60 include an enable switch 61, a joystick 62, linear switches 63, a mode switching button 64, a mode indicator 65, a pivot button 66, and an adjustment button 67.

The enable switch 61 is configured to enable or disable movement of the robot arm 50 by means of the joystick 62 and the linear switches 63 when pressed. Movement of the surgical instrument 1 by the robot arm 50 is enabled when the enable switch 61 is pressed while the arm operation unit 60 is grasped by an operator such as nurse, assistant, etc.

The joystick 62 is an operation tool configured to control movement of the surgical instrument 1 by the robot arm 50. The joystick 62 is an operation tool configured to control a moving direction and a moving speed of the robot arm 50. The robot arm 50 can be moved in accordance with a tilting direction and a tilting angle of the joystick 62.

The linear switches 63 are a switch for moving the surgical instrument 1 in the Z direction, which is a longitudinal direction of the surgical instrument 1. The linear switches 63 includes a linear switch 63*a* for moving the surgical instrument 1 in a direction in which the surgical instrument 1 is inserted into a patient P, and a linear switch 63*b* for moving the surgical instrument 1 in a direction in which the surgical instrument 1 is moved away from the patient P. The linear switch 63*a* and the linear switch 63*b* are constructed of a press-button switch.

Figures 7, 8:
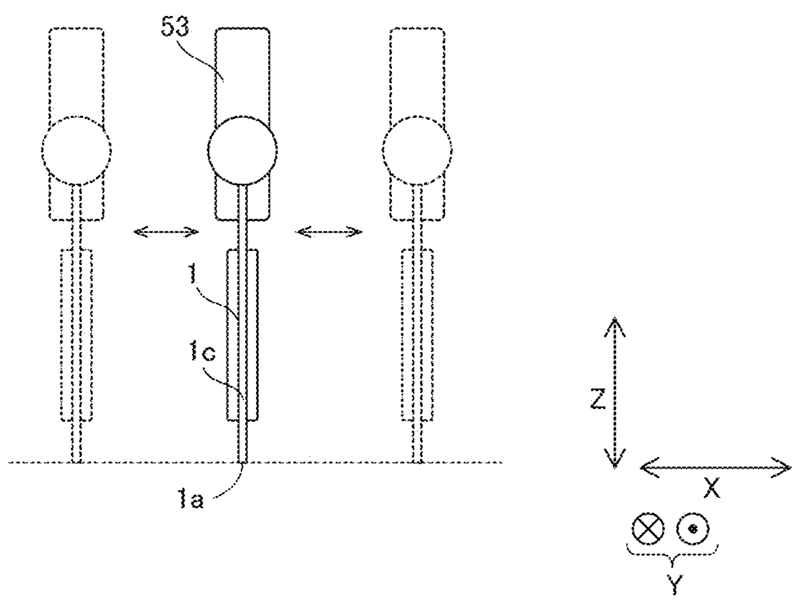
FIG. 7 is a diagram illustrating translational movement of the robot arm.
FIG. 8 is a diagram illustrating rotational movement of the robot arm.

The mode switching button 64 is a press-button switch for switching between a translation mode in which the surgical instrument 1 is translationally moved, and a rotation mode in which the surgical instrument 1 is rotated. As shown in FIG. 7, in the translation mode in which the robot arm 50 is translationally moved, the robot arm 50 can be moved so that the distal end 1*a* of the surgical instrument 1 can be moved in an X-Y plane. As shown in FIG. 8, in the rotation mode in which the robot arm 50 is rotated, in a case in which any pivot position PP is not stored in the storage 351, the robot arm 50 can be moved so that the forceps 2*b* can be rotated about a center of the forceps 2*b* of the instrument 2 as the surgical instrument 1 on the A11 axis or the distal end of the forceps 2*b* as a rotation axis, and in a case in which a pivot position PP is stored in the storage 351, the robot arm 50 can be moved so that the surgical instrument 1 can be rotated about the pivot position PP as a rotation axis. In this case, the surgical instrument 1 is rotated with the shaft 1*c* of the surgical instrument 1 being inserted into a trocar T. The mode switching button 64 is arranged on a surface on a Z-direction side of the arm operation unit 60.

The mode indicator 65 is configured to indicate which mode is selected. The mode indicator 65 is configured to light on to indicate the rotation mode, and to light off indicate the translation mode. The mode indicator 65 also serves as a pivot position indicator to indicate that the pivot position PP is set. The mode indicator 65 is arranged on the surface on the Z-direction side of the arm operation unit 60.

The pivot button 66 is a press-button switch configured to set the pivot position PP, which corresponds to the rotation axis of the surgical instrument 1 attached to the robot arm 50.

The adjustment button 67 is a button configured to optimize a position of the robot arm 50. After the pivot position PP is set with respect to the robot arm 50 to which the endoscope 3 is attached, when the adjustment button 67 is pressed positions of the other robot arms 50 and the arm base 40 is optimized. The adjustment button 67 is a button different from the enable switch 61.

(Remote Control Apparatus)

For example, as shown in FIG. 1, the remote control apparatus 200 is arranged in an operating room or outside the operating room. The remote control apparatus 200 includes operation units 110, foot pedals 120, a touch panel 130, a monitor 140, a support arm 150, a support bar 160, and an error reset button 161. The operation units 110 serves as a handle for operation that is configured to receive commands from an operator such as doctor.

(Operation Unit)

Figure 11:
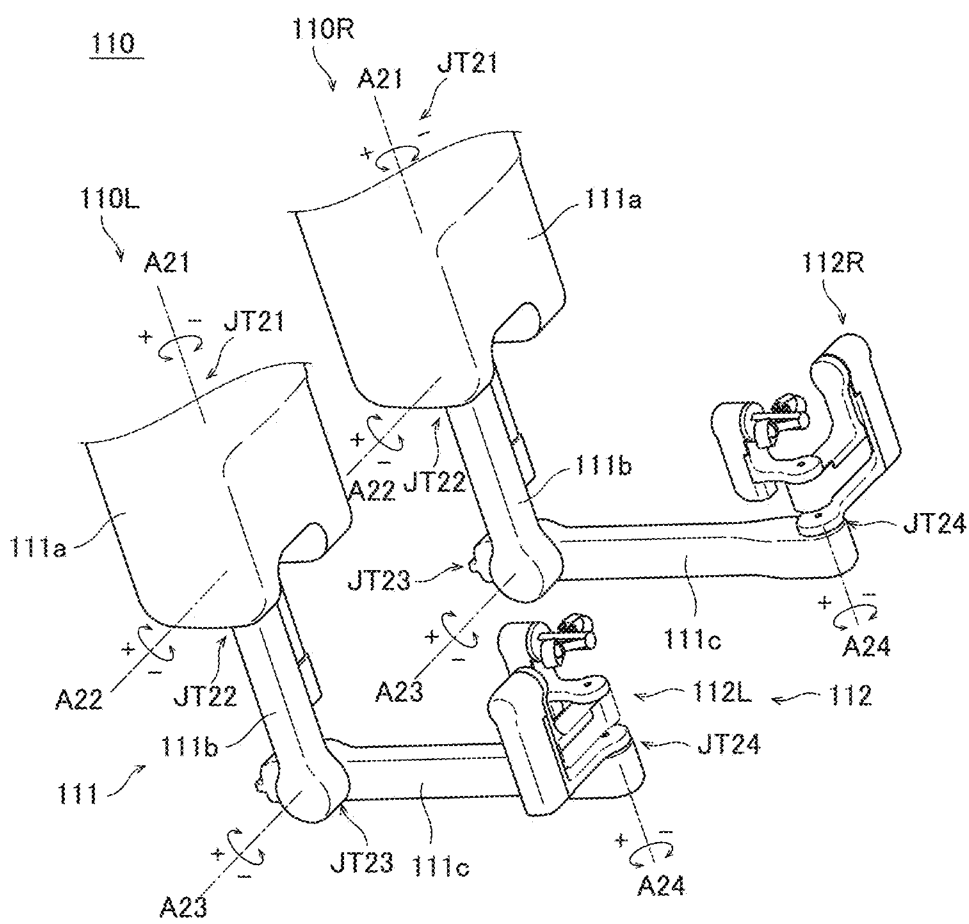
FIG. 11 is a diagram showing operation units according to the one embodiment.

As shown in FIG. 11, the operation units 110 are handle configured to manipulate the surgical instrument 1. Also, the operation units 110 are configured to accept operation of the operator on the surgical instruments 1. The operation units 110 include an operation unit 110L that is arranged on a left side from viewpoint of an operator such as doctor and is configured to be manually operated by operator's left hand, and an operation unit 110R that is arranged on a right side from viewpoint of the operator such as doctor and is configured to be manually operated by operator's right hand. The operation units 110 include arm parts 111 and wrist parts 112. The operation unit 110R includes an arm part 111R and a wrist part 112R. The operation unit 110L includes an arm part 111L and a wrist part 112L.

Figure 12:
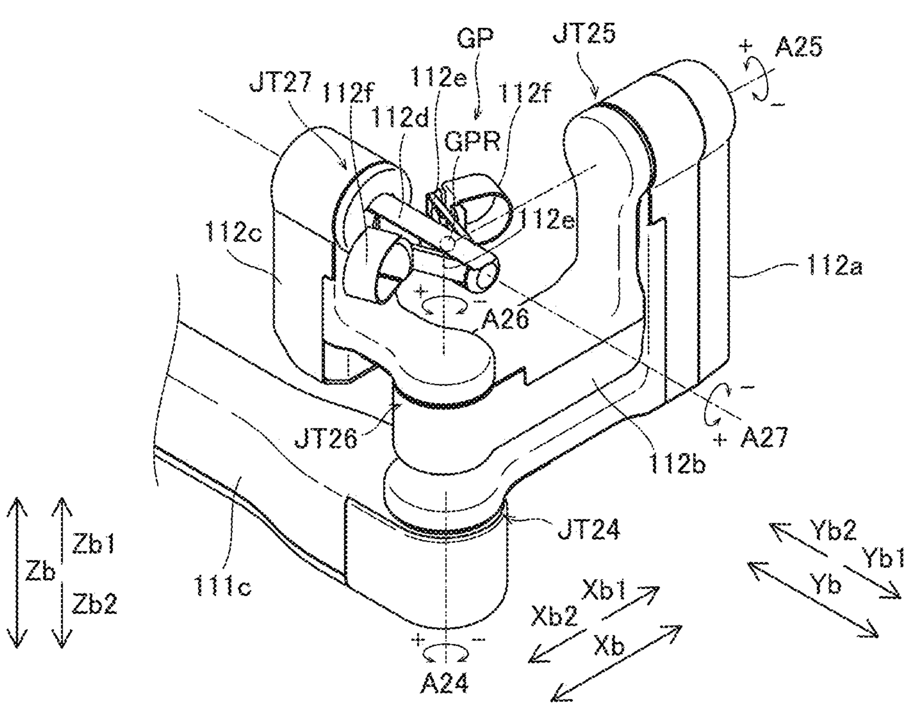
FIG. 12 is a diagram showing a right-hand side wrist part according to the one embodiment.
Figure 13:
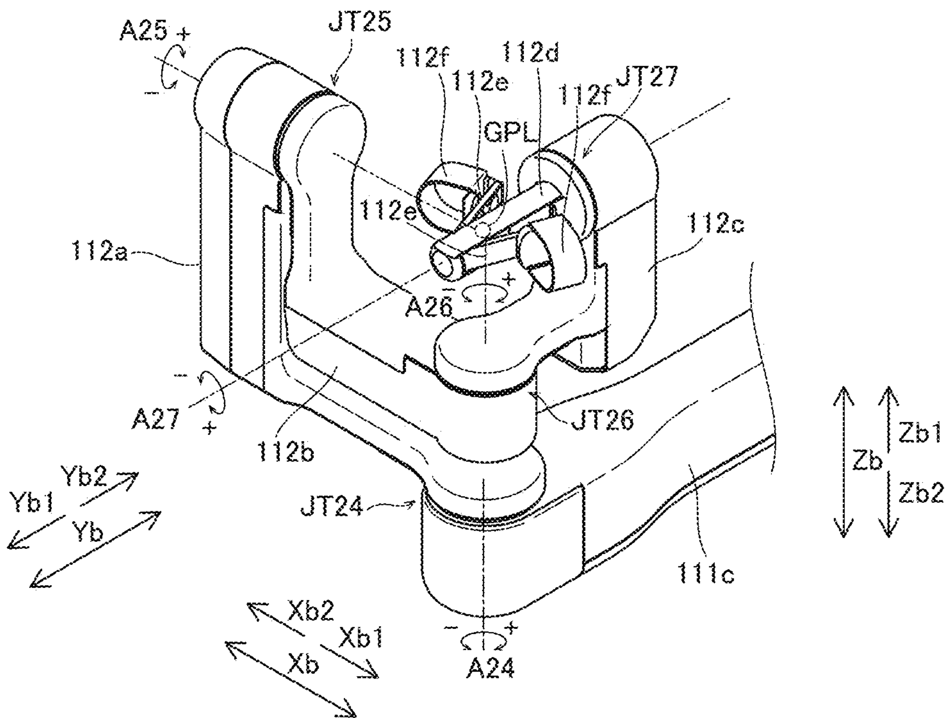
FIG. 13 is a diagram showing a left-hand side wrist part according to the one embodiment.

As shown in FIGS. 11, 12 and 13, the operation unit 110 includes joints JT21, JT22, JT23, JT24, JT25, JT26 and JT27. Axes A21, A22, A23, A24, A25, A26 and A27 are rotation axes of the joints JT21, JT22, JT23, JT24, JT25, JT26 and JT27.

(Arm)

The arm part 111 includes a link part 111*a*, a link part 111*b* and a link part 111*c*. An upper end side of the link part 111*a* is attached to the remote control apparatus 200 pivotably about the A21 rotation axis extending in a vertical direction. An upper end side of the link part 111*b* is attached to a lower part of the link part 111*a* pivotably about the A22 rotation axis extending in a horizontal direction. One end side of the link part 111*c* is attached to a lower part of the link part 111*b* pivotably about the A23 rotation axis extending in a horizontal direction. The wrist part 112 is attached to another end side of the link part 111*c* pivotably about the A24 rotation axis. The link part 111*a* is connected to the remote control apparatus 200 by the joint JT21. The link part 111*a* is connected to the link part 111*b* by the joint JT22. The link part 111*b* is connected to the link part 111*c* by the joint JT23. The arm part 111 supports the wrist part 112.

The wrist parts 112 include a wrist part 112R shown in FIG. 12 operated by an operator's right hand, and a wrist part 112L shown in FIG. 13 operated by an operator's left hand. A reference posture of the operation unit 110R is shown in FIG. 12, a reference posture of the operation unit 110L is shown in FIG. 13. A configuration of the wrist part 112R is similar to the wrist part 112L.

The wrist part 112 includes a link part 112*a*, a link part 112*b*, a link part 112*c*, and a grip part 112*d* configured to be gripped and operated by an operator (e.g., a doctor). The link part 112*a* can pivot about an A24 axis. The link part 112*b* is attached to the link part 112*a* pivotably about an A25 rotation axis. The link part 112*c* is attached to the link part 112*b* pivotably about an A26 rotation axis. The grip part 112*d* is attached to the link part 112*c* pivotably about an A27 rotation axis. The link part 112*a*, the link part 112*b* and the link part 112*c* have an L shape.

Each wrist part 112 includes a pair of grip members 112*e* configured to be opened and closed by the operator. The grip member 112*e* is formed of a thin plate-shaped lever, and near-side ends of the pair of grip members 112*e* are rotatably coupled to a near-side end of the grip part 112*d*. The grip members 112*e* include cylindrical finger insertion sections 112*f*. The operator can insert his or her fingers into the finger insertion sections 112*f*, and operate the wrist part 112. Base-side ends of the pair of grip member 112*e* are coupled to the grip part 112*d* so that opening angle between the Jaw 2*f* and the jaw 2*g* can be changed by increasing/decreasing an angle between the pair of grip members 112*e*. One of the grip members 112*e* includes a magnet, while the grip part 112*d* includes a Hall sensor. The magnet and the Hall sensor function as an angle detection sensor, and can provide an opening angle when the operator opens/closes the grip members 112*e*. One of the grip members 112*e* may include a Hall sensor, while the grip part 112*d* may include a magnet so that they form the angle detection sensor. Also, both the grip members 112*e* may include a magnet or a Hall sensor as a part of the angle detection sensor.

An intersection between rotation axes of the operation unit 110 is referred to as gimbal point GP. Specifically, the gimbal point GP is an intersection between the A24 axis, the A25 axis, the A26 axis and the A27 axis. The gimbal point GP is positioned in the grip part 112*d* to which the pair of grip members 112*e* are attached. Each of the operation unit 110L and the operation unit 110R has the gimbal point GP. A gimbal point of the operation unit 110R is defined as GPR. A gimbal point of the operation unit 110L is defined as GPL.

In the reference posture, the A24 axis and the A26 axis of the operation unit 110 extend in the Zb direction. The A25 axis extends in the Xb direction. The A27 axis extends in the Yb direction. As shown in FIG. 12, in the reference posture, the link part 112*a* and the link part 112*b* of the wrist part 112R arranged in an Xb-Zb plane, and is located on an Xb1 side with respect to the A27 axis. In the reference posture, the link part 112*c* arranged in an Yb-Zb plane. In the reference posture, the grip part 112*d* extend in the A27 axis.

In the reference posture, the link part 112*a* and the link part 112*b* of the wrist part 112L arranged in an Xb-Zb plane, and is located on an Xb2 side with respect to the A27 axis. In the reference posture, the link part 112*c* arranged in an Yb-Zb plane. In the reference posture, the grip part 112*d* extend in the A27 axis.

As shown in FIG. 1, the monitor 140 is a scope-type display device configured to display images captured by the endoscope 3. The monitor 140 includes a speaker 141. The doctor is notified of an error sound from the speaker 141 when an error occurs. The support arm 150 supports the monitor 140, and can adjust a height of the monitor 140 to a height of eyes of the operator such as doctor. The touch panel 130 is arranged on the support bar 160. When a head of the operator is detected by a sensor arranged in proximity to the monitor 140, the surgical robot 100 can accept manual operations from the remote control apparatus 200. The operator will manually operate the operation unit 110 and the foot pedals 120 while seeing of an affected area on the monitor 140. Commands can be provided to the remote control apparatus 200 in accordance with these manual operations. Instructions provided to the remote control apparatus 200 are transmitted to the surgical robot 100.

The error reset button 161 is arranged on the support bar 160. The error reset button 161 is configured to reset an error of the robotic surgical system 500. An exemplary error is an error of abnormal deviation.

(Foot Pedal)

Figure 14:
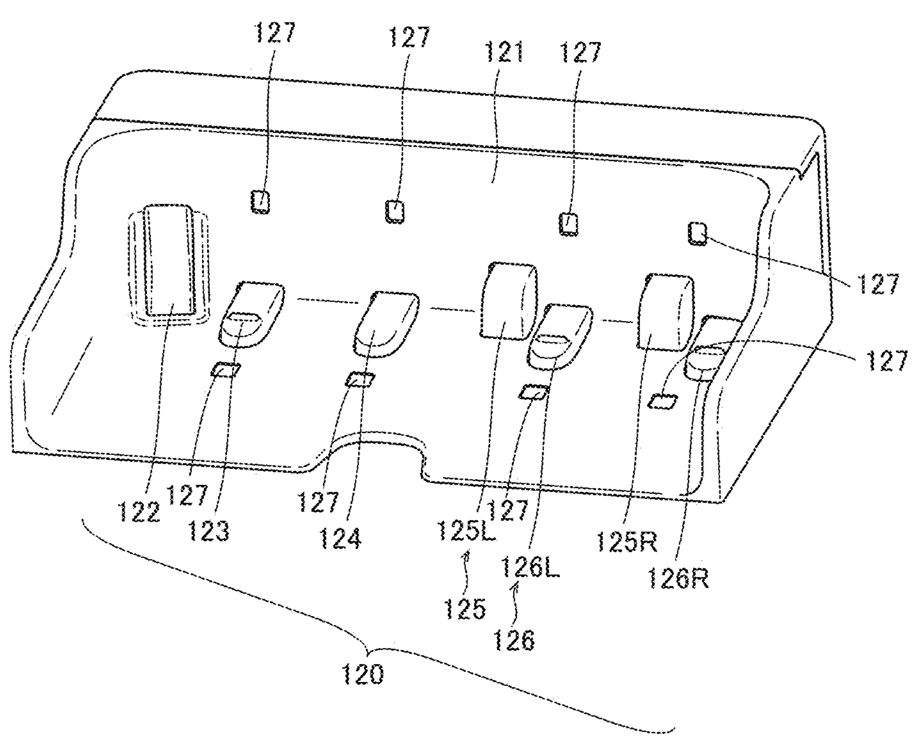
FIG. 14 is a perspective diagram showing a foot pedal according to the one embodiment.

As shown in FIG. 14, a plurality of foot pedals 120 configured to activate functions of the surgical instruments 1. The plurality of foot pedals 120 are provided in a base 121. The foot pedals 120 include a switching pedal 122, a clutch pedal 123, a camera pedal 124, incision pedals 125, coagulation pedals 126, and foot detectors 127. The switching pedal 122, the clutch pedal 123, the camera pedal 124, the incision pedals 125, the coagulation pedals 126 are configured to be operated by an operator's foot. Also, the incision pedals 125 include an incision pedal 125R corresponding to a right-side robot arm 50 and an incision pedal 125L corresponding to a left-side robot arm 50. Also, the coagulation pedals 126 include a coagulation pedal 126R corresponding to a right-side robot arm 50 and a coagulation pedal 126L corresponding to a left-side robot arm 50.

The switching pedal 122 is configured to switch between the robot arms 50 to be operated by the operation unit 110. The clutch pedal 123 is configured to activate a clutch function of temporally halting operation connection between the robot arm 50 and the operation unit 110. While the clutch pedal 123 is pressed by the operator, instructions provided by the operation unit 110 is not transmitted to the robot arm 50. While the camera pedal 124 is pressed by the operator, the robot arm 50 that holds the endoscope 3 can be operated through the operation unit 110. While the incision pedal 125 or the coagulation pedal 126 is pressed, an electric surgical apparatus is active.

The foot detectors 127 are configured to detect the operator's foot that operates the foot pedal 120. The foot detector 127 are arranged corresponding to the switching pedal 122, the clutch pedal 123, the camera pedal 124, the incision pedal 125L, the coagulation pedal 126L, the incision pedal 125R and the coagulation pedal 126R to detect a foot that hovers above their corresponding foot pedal 120. The foot detectors 127 are arranged on the base 121. Functions of the foot pedals 120 including the camera pedal 124 are not limited to operations through a pedal configured to be pressed by an operator's foot as discussed in this embodiment, and inputs such as hand switches may be provided in the operation unit 110 to be manually operated by an operator's hand instead of the foot pedals, for example.

(Vision Unit and Image Processing Unit)

As shown in FIG. 1, a cart 210 holds a vision unit 300 and an image processing unit 400. The image processing unit 400 is configured to process images captured by the endoscope 3. A display 220 is arranged on the cart 210. The display 220 is configured to display images captured by the endoscope 3. An error reset button 230 and a speaker 240 are arranged on a vision unit 300. The error reset button 230 is configured to reset an error of the robotic surgical system 500. An exemplary error is an error of abnormal deviation. The nurse and assistant are notified of an error sound from the speaker 240 when an error occurs.

(Configuration of Control System)

As shown in FIG. 15, the robotic surgical system 500 includes a first controller 310, an arm controller 320, a positioner controller 330, operation controllers 340 and a second controller 350. In addition, the robotic surgical system 500 includes a storage 311 connected to the first controller 310, and a storage 351 connected to the second controller 350. The operation controller 340 is an example of a controller and a control unit.

The first controller 310 is accommodated in the medical cart 10, and configured to communicate with the arm controller 320 and the positioner controller 330 so that the robotic surgical system 500 is entirely controlled. Specifically, the first controller 310 is configured to control the arm controller 320, the positioner controller 330 and the operation controllers 340 by using the communications with them. The first controller 310 is connected to the arm controller 320, the positioner controller 330 and the operation controllers 340 through LAN, etc. The first controller 310 is arranged in the medical cart 10.

Each of the plurality of robot arms 50 includes the arm controller 320. In other words, a plurality of arm controllers 320 the number of which corresponds to the number of the plurality of robot arms 50 are included in the medical cart 10.

The input 22 is connected to the first controller 310 through LAN, etc. The status indicator 41, the arm status indicator 42, the operating handle 23, the throttle grip 23*a*, the joystick 22*b*, the stabilizer 24 and the electric cylinder 25 are connected to the positioner controller 330 through a wiring line 360 by means of a communication network that can share information with them by using serial communication. Although all of the status indicator 41, arm status indicator 42, etc. are connected to each other through one wiring line 360 in FIG. 15, wiring lines 360 are actually provided to each of the status indicator 41, the arm status indicator 42, the operating handle 23, the throttle grip 23*a*, the joystick 22*b*, the stabilizer 24 and the electric cylinder 25.

Figure 16:
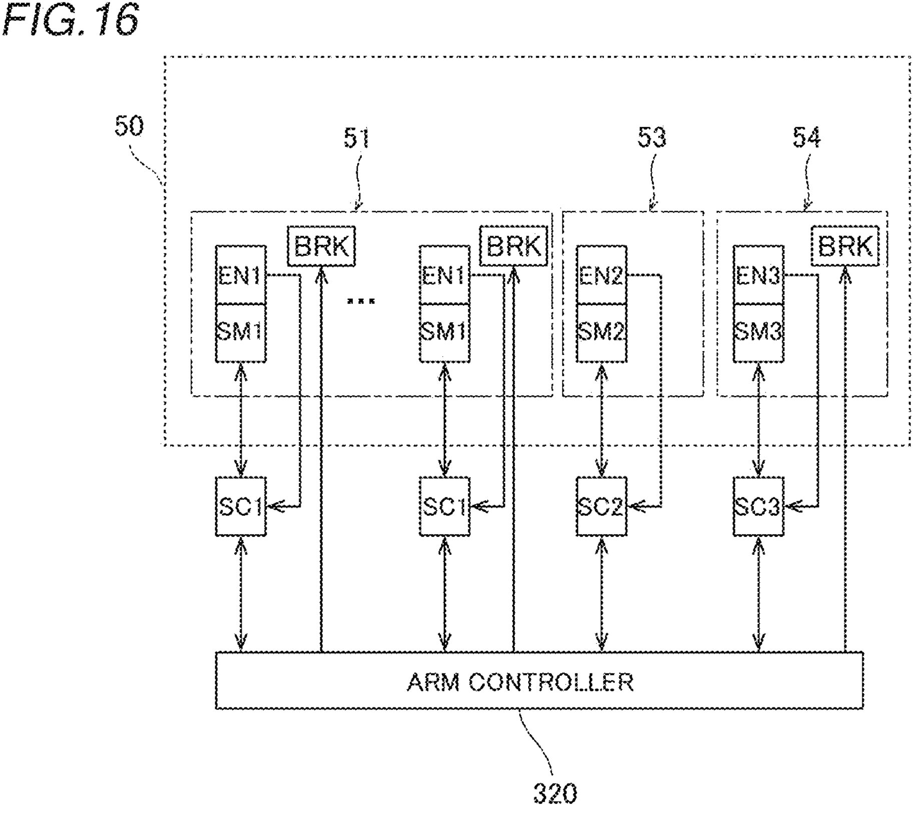
FIG. 16 is a control block diagram of the robot arm according to the one embodiment.

As shown in FIG. 16, each arm 51 includes a plurality of servomotors SM1, a plurality of encoders EN1 and a plurality of speed reducers corresponding to the Joints JT1, JT2, JT3, JT4, JT5, JT6 and JT7. The encoder EN1 is configured to detect a rotation angle of the servomotor SM1. The speed reducer is configured to reduce a rotation of the servomotor SM1 whereby increasing its torque. A servo controller SC1 is configured to control the servomotor SM1, and is arranged in the medical cart 10 adjacent to the arm controller 320. Also, the encoder EN1 is configured to detect the rotation angle of the servomotor SM1, and is electrically connected to the servo controller SC1.

The second link part 53 includes a servomotor SM2 configured to rotate a driven member arranged in a driven unit 2*a* of the surgical instrument 1, an encoder EN2, and a speed reducer. The encoder EN2 is configured to detect a rotation angle of the servomotor SM2. The speed reducer is configured to reduce a rotation of the servomotor SM2 whereby increasing its torque. The medical cart 10 includes a servo controller SC2 configured to control the servomotor SM2 for driving the surgical instrument 1. The encoder EN2 for detecting the rotation angle of the servomotor SM2 is electrically connected to the servo control unit SC2. Note that a plurality of servomotors SM2, a plurality of encoders EN2 and a plurality of servo controllers SC2 are included.

The translation mechanism 54 includes a servomotor SM3 configured to translationally move the surgical instrument 1, an encoder EN3, and a speed reducer. The encoder EN3 is configured to detect a rotation angle of the servomotor SM3. The speed reducer is configured to reduce a rotation of the servomotor SM3 whereby increasing its torque. The medical cart 10 includes a servo controller SC3 configured to control the servomotor SM3 for translationally moving the surgical instrument 1. The encoder EN3 for detecting the rotation angle of the servomotor SM3 is electrically connected to the servo control unit SC3.

The first controller 310 is configured to generate instruction values that specify positions of the servomotor SM1, SM2 and SM3 in accordance with manual operation that is received by the remote control apparatus 200, and to drive the servomotor SM1, SM2 and SM3 in accordance with the instruction values. If any of differences between instruction values and positions of servomotor SM1, SM2 and SM3 detected by sensors becomes greater than an allowable range, the first controller 310 determines an error of abnormal deviation.

Figure 17:
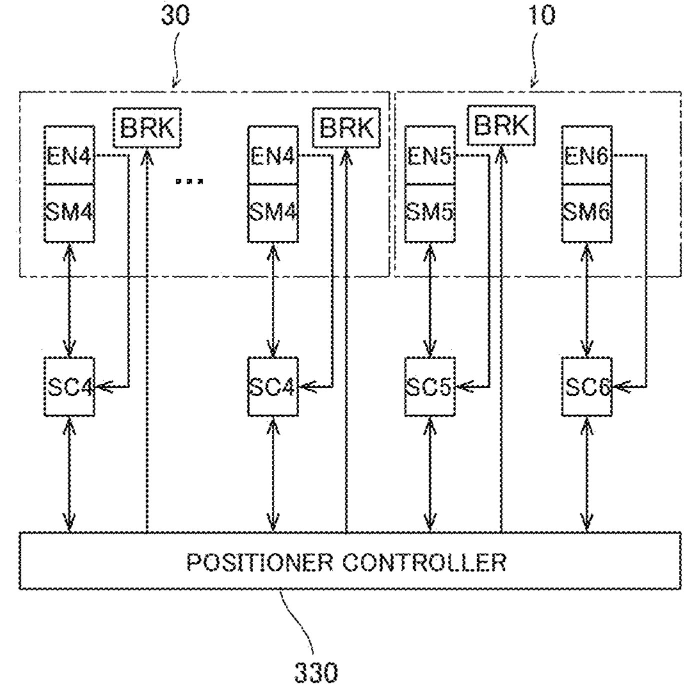
FIG. 17 is a control block diagram of a positioner and the medical cart according to the one embodiment.

As shown in FIG. 17, the positioner 30 includes a plurality of servomotors SM4, a plurality of encoders EN4 and a plurality of speed reducers corresponding to a plurality of joints 33 of the positioner 30. Each encoder EN4 is configured to detect a rotation angle of the servomotor SM4. The speed reducer is configured to reduce a rotation of the servomotor SM4 whereby increasing its torque.

The medical cart 10 includes wheels including front wheels as driving wheels, and rear wheels configured to be steered by manually operating the operating handle 23. The rear wheels are arranged closer to the operating handle 23 with respect to the front wheels. The medical cart 10 includes a servomotor SM5 configured to drive the front wheels of the medical cart 10, an encoder EN5, speed reducers, and brakes BRK. The speed reducer is configured to reduce a rotation of the servomotor SM5 whereby increasing its torque. Also, the operating handle 23 of the medical cart 10 includes a potentiometer P1 shown in FIG. 3, and the servomotor SM5 of the front wheels can be driven in accordance with a rotation angle detected by the potentiometer P1 in response to a twisting amount of the throttle grip 23*a*. The rear wheels of the medical cart 10 have a twin-wheel type structure, and the rear wheels can be steered in accordance with a rightward/leftward turn of the operating handle 23. Also, the operating handle 23 of the medical cart 10 includes a potentiometer P2 shown in FIG. 3 on a turning shaft, and the rear wheel of the medical cart 10 is provided with a servomotor SM6, an encoder EN6, and speed reducers. The speed reducer is configured to reduce a rotation of the servomotor SM6 whereby increasing its torque. The servomotor SM6 can be driven in accordance with a rotation angle detected by the potentiometer P2 in response to a rightward/leftward turning amount of the operating handle 23. In other words, power is assisted by the servomotor SM6 when the rear wheels are steered by turning the operating handle 23 rightward or leftward.

The medical cart 10 can be moved forward or rearward by driving the front wheels. Also, the medical cart 10 can be turned rightward or leftward by steering the rear wheels by turning the operating handle 23 of the medical cart 10.

As shown in FIG. 17, the medical cart 10 includes servo controllers SC4 configured to control the servomotors SM4 for moving the positioner 30. Also, the encoder EN4 is configured to detect the rotation angle of the servomotor SM4, and is electrically connected to the servo controller SC4. The medical cart 10 includes a servo controller SC5 configured to control the servomotor SM5 for driving the front wheels of the medical cart 10. The encoder EN5 for detecting the rotation angle of the servomotor SM5 is electrically connected to the servo control unit SC5. The medical cart 10 includes a servo controller SC6 configured to control the servomotor SM6 for power assistance to steering of the rear wheels of the medical cart 10. The encoder EN6 for detecting the rotation angle of the servomotor SM6 is electrically connected to the servo control unit SC6.

As shown in FIGS. 16 and 17, the joints JT1, JT2, JT3, JT4, JT5, JT6 and JT7 of the arm 51, and the joints 33 of the positioner 30 include their brake BRK. Also, the front wheels of the medical cart 10, the arm base 40 and the translation mechanism 54 include their brake BRK. The arm controller 320 is configured to one-directionally transmit control signals to the brakes BRK of the joints JT1, JT2, JT3, JT4, JT5, JT6 and JT7 of the arm 51, and the translation mechanism 54. The control signals are configured to indicate on/off of the brakes BRK. The signals indicating on of the brakes BRK include a signal that instructs the brake BRK to keep activating. The control signals transmitted from the positioner controller 330 to the brakes BRK included in the joints 33 of the positioner 30 and the arm base 40 are configured similar to the control signals transmitted from the arm controller. On startup, all the brakes BRK of the arm base 40, the arm 51 and the translation mechanism 54 are turned off but the servomotors SM are driven to keep postures of the robot arm 50 and the arm base 40 against gravity. If an error occurs in the robotic surgical system 500, the brakes BRK included in the arm base 40, the arm 51 and the translation mechanism 54 are turned on. When the error in the robotic surgical system 500 is reset, the brakes BRK included in the arm base 40, the arm 51 and the translation mechanism 54 are turned off. When shutdown operation is performed in the robotic surgical system 500 is reset, the brakes BRK included in the arm base 40, the arm 51 and the translation mechanism 54 are turned on. The brakes BRK of the front wheels of the medical cart 10 are constantly turned on, and the brakes BRK are deactivated only when the enable switch 23*b* of the medical cart 10 is kept pressed. Also, the brakes BRK of the joints 33 of the positioner 30 are constantly turned on, and the brakes BRK are deactivated only when the enable switch 22*c* of the medical cart 10 is kept pressed.

Figure 18:
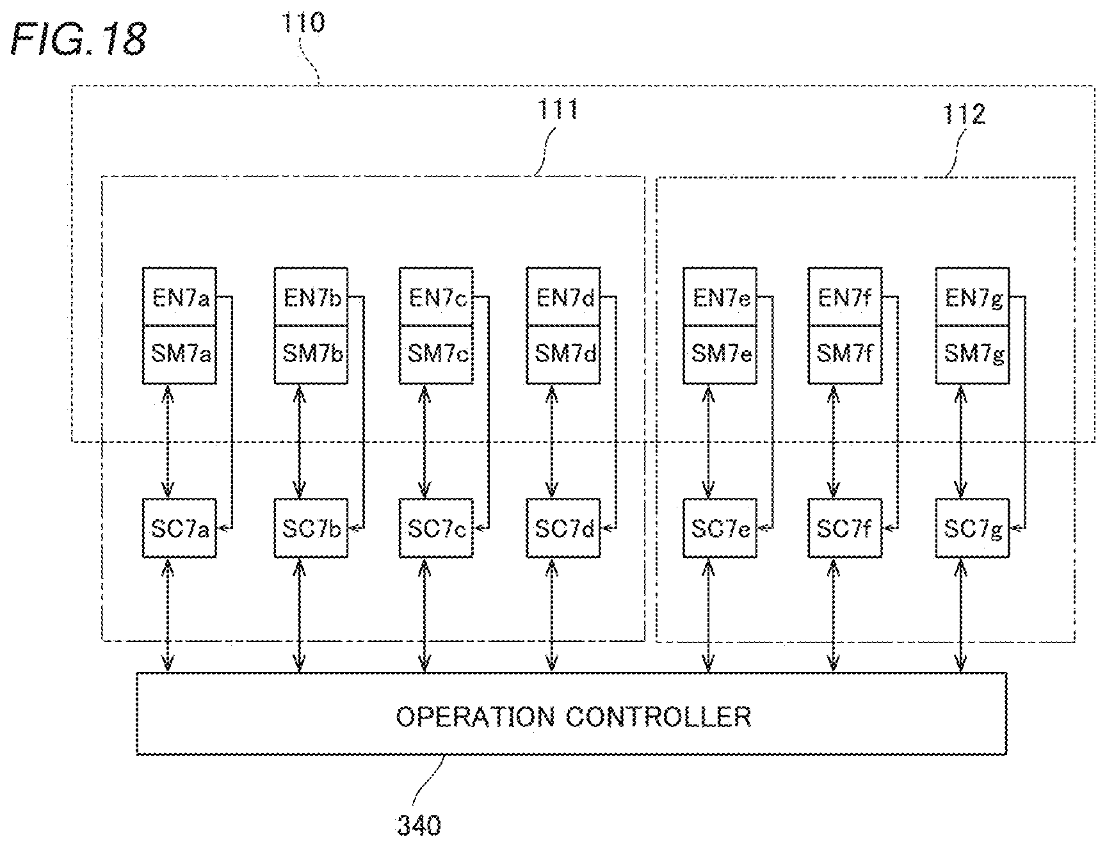
FIG. 18 is a control block diagram of the operation unit according to the one embodiment.

As shown in FIG. 18, the joints JT21, JT22, JT23, JT24, JT25, JT26 and JT27 of the operation unit 110 includes servomotors SM7*a*, SM7*b*, SM7*c*, SM7*d*, SM7*e*, SM7*f* and SM7*g*, respectively. Also, servo controllers SC7*a*, SC7*b*, SC7*c*, SC7*d*, SC7*e*, SC7*f* and SC7*g* configured to control the servomotors are provided. Encoders EN7*a*, EN7*b*, EN7*c*, EN7*d*, EN7*e*, EN7*f* and EN7*g* for detecting rotation angles of the servomotors are electrically connected to the servo controllers. Each of the operation unit 110L and the operation unit 110R includes the servomotors, the servo controllers and the encoders. The servomotors SM7*a*, SM7*b*, SM7*c*, SM7*d*, SM7*e*, SM7*f* and SM7*g* are configured to assist the operation of the operator. The servomotors SM7*a*, SM7*b*, SM7*c*, SM7*d*, SM7*e*, SM7*f* and SM7*g* are examples of drivers.

The operation controllers 340 is configured to control the servomotors so that torques are produced to cancel out gravitational torques applied to the rotation axes of the servomotors in postures of the operation units 110. Accordingly, the operator can manually operate the operation units 110 by relatively small forces.

As shown in FIG. 15, the first controller 310 is configured to control the robot arm 50 in accordance with manual operations received by the arm operation unit 60. For example, the first controller 310 is configured to control the robot arm 50 in accordance with manual operations received by the joystick 62 of the arm operation unit 60. Specifically, the arm controller 320 provides an input signal provided from the joystick 62 to the first controller 310. The first controller 310 generates position commands based on the received input signal and the rotation angles detected by the encoders EN1, and provides the position commands to the servo controllers SC1 via the arm controller 320. The servo controllers SC1 generate current commands based on the position commands provided from the arm controller 320 and the rotation angles detected by the encoders EN1, and provide the current commands to the servomotors SM1. Accordingly, the robot arm 50 is moved in accordance with an operation command provided to the joystick 62.

The first controller 310 controls the robot arm 50 based on an input signal from the linear switch 63 of the arm operation unit 60. Specifically, the arm controller 320 provides an input signal provided from the linear switch 63 to the first controller 310. The first controller 310 generates position commands based on the received input signal and the rotation angles detected by the encoder EN1 or EN3, and provides the position commands to the servo controller SC1 or SC3 via the arm controller 320. The servo controller SC1 or SC3 generate current commands based on the position commands provided from the arm controller 320 and the rotation angles detected by the encoder EN1 or EN3, and provide the current commands to the servomotor SM1 or SM3. Accordingly, the robot arm 50 is moved in accordance with an operation command provided to the linear switch 63.

The medical cart 10 includes the positioner controller 330. The positioner controller 330 is configured to control the positioner 30 and the medical cart 10. The positioner 30 includes a plurality of servomotors SM4, a plurality of encoders EN4 and a plurality of speed reducers corresponding to a plurality of joints 33 of the positioner 30. The medical cart 10 includes the servo controllers SC4 configured to control the servomotors SM4 of the positioner 30. The medical cart 10 includes servomotors SM5 and SM6 configured to drive the front wheels of the medical cart 10, the encoders EN5 and EN6, speed reducers, the servo controllers SC5 and SC6, and brakes BRK.

The operation controllers 340 are provided in a main body of the remote control apparatus 200. The operation controllers 340 are configured to control the operation units 110. The operation controllers 340 are associated with both the left-hand side operation unit 110L and the right-hand side operation unit 110R as shown in FIG. 15. The operation unit 110 includes servomotors SM, encoders EN and speed reducers corresponding to the plurality of joints JT21 to JT27 of the operation unit 110. The servo controllers SC configured to control the servomotors SM of the operation unit 110 is provided in the main body of the remote control apparatus 200 adjacent to the operation controllers 340.

As shown in FIG. 15, the vision unit 300 and the image processing unit 400 are connected to the first controller 310 through LAN. The display 220 is connected to the vision unit 300.

Figure 19:
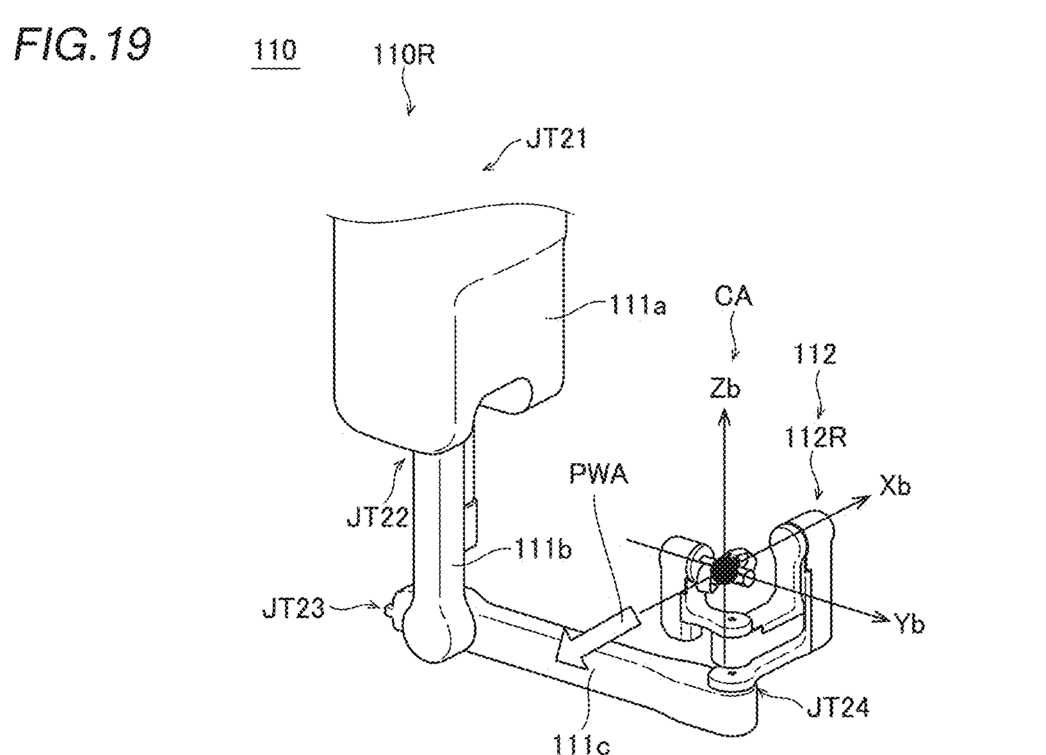
FIG. 19 is a view illustrating application of a force to the operation unit in a Cartesian coordinate system in the one embodiment.

As shown in FIG. 19, a three-axis Cartesian coordinate system CA, which has three axes orthogonal to each other, is defined in the operation unit 110. The three axes of the Cartesian coordinate system CA include Xb, Yb and Zb directions. The Cartesian coordinate system CA has an origin at a position of the grip part 112*d* when operation unit is in a reference posture. Although the operation unit 110R is illustrated for convenience in FIG. 19, the same goes for the operation unit 110L.

In this embodiment, the operation controller 340 is configured to control the servomotors so as to apply a force PWA to the operation unit 110 in a direction opposite to a direction of the operation of the operation unit in the Cartesian coordinate system CA having three axes orthogonal to each other. Specifically, the operation controller 340 is configured to control at least one of the servomotors SM7*a*, SM7*b*, SM7*c*, SM7*d*, SM7*e*, SM7*f*, and SM7*g* so as to apply a force PWA in a direction opposite to a direction of the operation of the operation unit 110 in the Cartesian coordinate system CA. More specifically, the operation controller 340 is configured to apply the force PWA by controlling the servomotors SM7*a*, SM7*b* and SM7*c*, which are provided to three joints JT21, JT22 and JT23 that are connected closer to a proximal end of the operation unit 110 in the plurality of joints JT21, JT22, JT23, JT24, JT25, JT26 and JT27. In other words, the operation controller 340 is configured to apply the force PWA by controlling the servomotors SM7*a*, SM7*b* and SM7*c* of the joints JT21, JT22 and JT23, which are configured to move the surgical instrument 1 by using the robot arm 50. In an exemplary case shown in FIG. 19, the direction of the operation of the operation unit 110 is a positive direction of the direction Xb, and the force PWA is applied to the operation unit in a negative direction of the Xb direction. The proximal end of the operation unit 110 refers to the link part 111*a* side of the operation unit.

The operation controller 340 is configured to acquire the direction of the operation of the operation unit 110 in the Cartesian coordinate system CA based on at least one of detection results of rotation angles of the encoders EN7*a*, EN7*b*, EN7*c*, EN7*d*, EN7*e*, EN7*f* and EN7*g*. The operation controller 340 is configured to generate current command values for applying the force PWA in the direction opposite to the acquired direction of the operation of the operation unit 110, and to output the current command values to the servomotors SM7*a*, SM7*b* and SM7*c*. When the servomotors SM7*a*, SM7*b* and SM7*c* are driven based on the current command values, a resultant force of forces generated by driving the servomotors SM7*a*, SM7*b* and SM7*c* is applied as the force PWA to the operation unit.

Figures 20, 21:
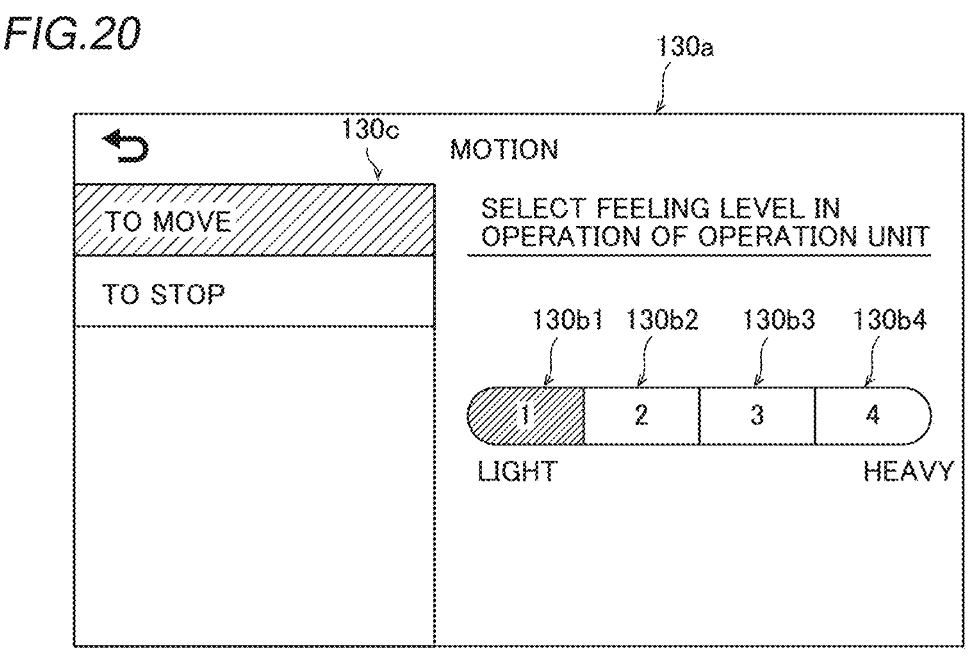
FIG. 20 is a diagram showing an acceptor for changing a level of the force according to the one embodiment.
FIG. 21 is a graph showing an operation parameter according to the one embodiment.

In this embodiment, the robotic surgical system 500 includes an acceptor 130*a* configured to accept a force-changing operation to change a level of the force PWA of the operator as shown in FIG. 20. The level of the force PWA can be changed to one of a plurality of levels. The acceptor 130*a* includes level selectors 130*b*1, 130*b*2, 130*b*3 and 130*b*4 corresponding to the plurality of levels. The level selector 130*b*1, 130*b*2, 130*b*3 and 130*b*4 correspond to a light level, a slightly light level, a slightly heavy level, and a heavy level, respectively. The operation controller 340 is configured to change the level of the force PWA in accordance with the force-changing operation for changing the level of the force PWA accepted by the acceptor 130*a*. The acceptor 130*a* is an example of a first acceptor and an example of a second acceptor.

The acceptor 130*a* includes a level-item-to-be-changed selector 130*c* for selecting a level item to be changed from a level of the force PWA and a level of the braking force PWB, which will be described later. The level selectors 130*b*1, 130*b*2, 130*b*3 and 130*b*4 are configured to accept a level-changing operation for changing a level of an item that is selected by using the level-item-to-be-changed selector 130*c*. For example, if an item "To Move" button as the level-item-to-be-changed selector 130*c* is pressed, the level selector 130*b*1, 130*b*2, 130*b*3 and 130*b*4 can accept the level-changing operation for changing a level of the force PWA. Also, for example, if an item "To Stop" button as the level-item-to-be-changed selector 130*c* is pressed, the level selector 130*b*1, 130*b*2, 130*b*3 and 130*b*4 can accept the level-changing operation for changing a level of the braking force PWB.

For example, the acceptor 130*a* is displayed on the touch panel 130 of the remote control apparatus 200. The level selectors 130*b*1, 130*b*2, 130*b*3 and 130*b*4, and the level-item-to-be-changed selector 130*c* are touch buttons.

In this embodiment, as shown in FIG. 21, the operation controller 340 is configured to determine an operation parameter PA of the servomotors SM7*a*, SM7*b* and SM7*c* based on an operation velocity V of the operation unit 110, and to control the servomotor SM7*a*, controls SM7*b* and SM7*c* so as to apply the force PWA based on the operation parameter PA determined.

Specifically, the operation controller 340 is configured to increase, if an absolute value of the operation velocity V of the operation unit 110 is not greater than a first threshold value TH1, an absolute value of the operation parameter PA as the absolute value of the operation velocity V of the operation unit 110 increases, and to fix the absolute value of the operation parameter PA at a maximum value if the absolute value of the operation velocity V of the operation unit 110 is greater than the first threshold value TH1. That is, if the absolute value of the operation velocity V of the operation unit 110 is in a range from zero to the first threshold value TH1, the absolute value of the operation parameter PA linearly increases from zero to the maximum value of the operation parameter PA as the absolute value of the operation velocity V of the operation unit 110 increases. After the absolute value of the operation velocity V of the operation unit 110 becomes greater than the first threshold value TH1, the absolute value of the operation parameter PA is fixed at the maximum value.

In FIG. 21, a solid line represents the operation parameter PA in a case in which the level selector 130*b*1 is pressed. A dotted line represents the operation parameter PA in a case in which the level selector 130*b*2 is pressed. A single-dot dashed line represents the operation parameter PA in a case in which the level selector 130*b*3 is pressed. A double-dot dashed line represents the operation parameter PA in a case in which the level selector 130*b*4 is pressed. A gradient of the operation parameter PA, and the maximum value of the absolute value of the operation parameter PA become greater as the selected level of the force PWA becomes heavier.

The operation parameter PA is viscous friction force, for example. The servomotors SM7*a*, SM7*b* and SM7*c* are controlled so as to apply the force PWA corresponding to the viscous friction force.

The operation controller 340 is configured to acquire the operation velocity V of the operation unit 110 in the Cartesian coordinate system CA based on at least one of detection results of rotation angles of the encoders EN7*a*, EN7*b*, EN7*c*, EN7*d*, EN7*e*, EN7*f* and EN7*g*. The operation controller 340 is configured to determine the operation parameter PA in accordance with the acquired operation velocity V of the operation unit 110 and the selected level of the force PWA. For example, the operation controller 340 can determine the operation parameter PA by using information such as a table that maps the operation velocity V of the operation unit 110, the level of the force PWA, and the operation parameter PA correspondingly to a graph shown in FIG. 21.

Figure 22:
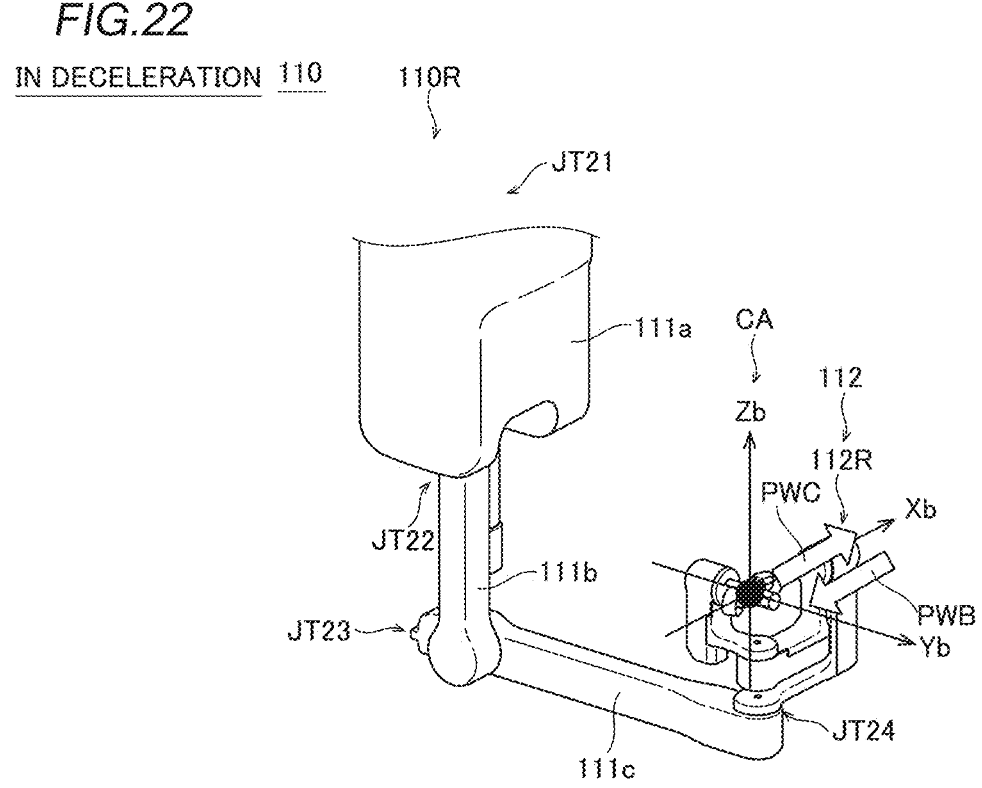
FIG. 22 is a view illustrating application of a braking force to the operation unit in deceleration of the operation unit in the Cartesian coordinate system in the one embodiment.
Figure 23:
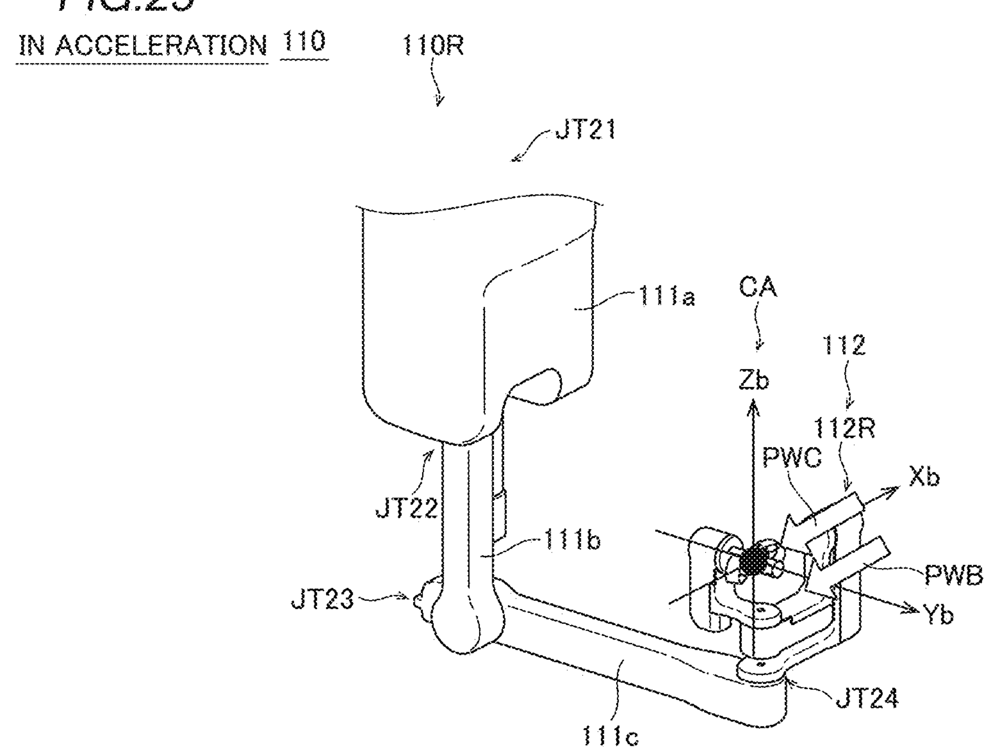
FIG. 23 is a view illustrating application of a braking force to the operation unit in acceleration of the operation unit in the Cartesian coordinate system in the one embodiment.

In this embodiment, as shown in FIGS. 22 and 23, the operation controller 340 is configured to control the servomotors SM7*a*, SM7*b* and SM7*c* so as to apply the braking force PWB in the Cartesian coordinate system CA in deceleration and/or acceleration of the operation of the operation unit 110. Specifically, the operation controller 340 is configured to control at least one of the servomotors SM7*a*, SM7*b* and SM7*c* so as to apply the braking force PWB in a direction opposite to a direction of an inertial force PWC applied to the operation unit 110 in the Cartesian coordinate system CA in deceleration of the operation of the operation unit 110. Also, the operation controller is configured to control at least one of the servomotors SM7*a*, SM7*b* and SM7*c* so as to apply the braking force PWB to the operation unit in the direction same as a direction of the inertial force PWC applied to the operation unit 110 in the Cartesian coordinate system CA in acceleration of the operation of the operation unit 110. In an exemplary case shown in FIG. 22, the direction of the inertial force PWC applied to the operation unit 110 in the deceleration is the positive direction of the direction Xb, and the braking force PWB is applied to the operation unit in the negative direction of the Xb direction. In an exemplary case shown in FIG. 23, the direction of the inertial force PWC applied to the operation unit 110 in the acceleration is the negative direction of the direction Xb, and the braking force PWB is applied to the operation unit in the negative direction of the Xb direction.

The operation controller 340 is configured to acquire an acceleration of the operation unit 110 in the Cartesian coordinate system CA based on at least one of detection results of rotation angles of the encoders EN7*a*, EN7*b*, EN7*c*, EN7*d*, EN7*e*, EN7*f* and EN7*g*. Subsequently, the operation controller 340 determines whether the operation of the operation unit 110 is in deceleration or acceleration based on the acquired acceleration of the operation unit 110. If the operation of the operation unit 110 is in deceleration, the operation controller 340 generates current command values for applying the braking force PWB in the direction opposite to the inertial force PWC applied to the operation unit 110, and outputs the current command values to the servomotors SM7*a*, SM7*b* and SM7*c*. Also, if the operation of the operation unit 110 is in acceleration, the operation controller 340 generates current command values for applying the braking force PWB in the direction same as the inertial force PWC applied to the operation unit 110, and outputs the current command values to the servomotors SM7*a*, SM7*b* and SM7*c*. When the servomotors SM7*a*, SM7*b* and SM7*c* are driven based on the current command values, a resultant force of forces generated by driving the servomotors SM7*a*, SM7*b* and SM7*c* is applied as the braking force PWB to the operation unit.

Figure 24:
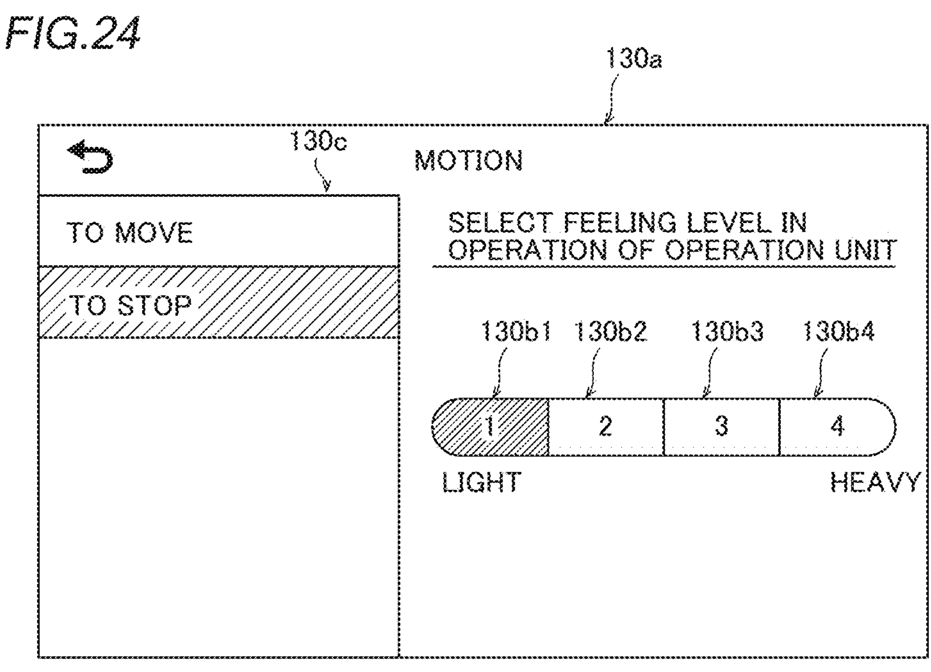
FIG. 24 is a diagram showing an acceptor for changing a level of the braking force according to the one embodiment.

In this embodiment, as shown in FIG. 24, the acceptor 130*a* is configured to accept a braking-force-changing operation to change a level of the braking force PWB of the operator. The operation controller 340 is configured to change the level of the braking force PWB in accordance with the force-changing operation for changing the level of the braking force accepted by the acceptor 130*a*.

Figure 25:
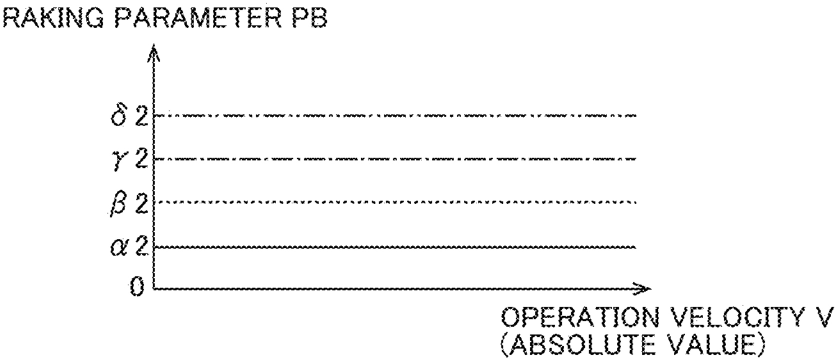
FIG. 25 is a graph showing an operation parameter in deceleration of the operation unit according to the one embodiment.
Figure 26:
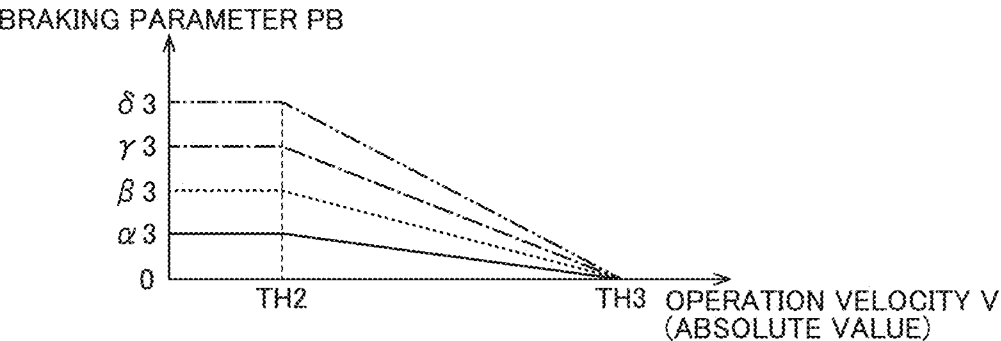
FIG. 26 is a graph showing an operation parameter in acceleration of the operation unit according to the one embodiment.

In this embodiment, as shown in FIGS. 25 and 26, the operation controller 340 is configured to determine a braking parameter PB of the servomotors SM7*a*, SM7*b* and SM7*c* in deceleration and/or acceleration of the operation of the operation unit 110, and to control the servomotor SM7*a*, controls SM7*b* and SM7*c* so as to apply the braking force PWB based on the braking parameter PB determined.

Specifically, as shown in FIG. 25, the operation controller 340 is configured to fix the braking parameter PB at a constant value in the deceleration of the operation of the operation unit 110. That is, in the deceleration of the operation of the operation unit 110, the braking parameter PB is fixed at the constant value irrespective of the operation velocity V of the operation unit 110.

In FIG. 25, a solid line represents the braking parameter PB in the deceleration in a case in which the level selector 130*b*1 is pressed. A dotted line represents the braking parameter PB in the deceleration in a case in which the level selector 130*b*2 is pressed. A single-dot dashed line represents the braking parameter PB in the deceleration in a case in which the level selector 130*b*3 is pressed. A double-dot dashed line represents the braking parameter PB in the deceleration in a case in which the level selector 130*b*4 is pressed. A value of the braking parameter PB becomes greater as the selected level of the braking force PWB becomes heavier.

Also, as shown in FIG. 26, the operation controller 340 is configured, in the acceleration of the operation of the operation unit 110, to fix the braking parameter PB at a maximum value if the absolute value of the operation velocity V of the operation unit 110 is not greater than a second threshold value TH2, to reduce the braking parameter PB as the operation velocity V of the operation unit 110 increases if the absolute value of the operation velocity V of the operation unit 110 is greater than the second threshold value TH2 and not greater than a third threshold value TH3, and to set the braking parameter PB zero if the absolute value of the operation velocity V of the operation unit 110 is greater than the third threshold value TH3. That is, if the absolute value of the operation velocity V of the operation unit 110 is in a range from zero to the second threshold value TH2, the braking parameter PB is fixed at the maximum value. That is, if the absolute value of the operation velocity V of the operation unit 110 is in a range from the second threshold value TH2 to the third threshold value TH3, the absolute value of the braking parameter PB linearly increases from the maximum value to zero as the absolute value of the operation velocity V of the operation unit 110 increases. After the absolute value of the operation velocity V of the operation unit 110 becomes greater than the third threshold value TH3, the braking parameter PB is fixed at zero.

In FIG. 26, a solid line represents the braking parameter PB in the acceleration in a case in which the level selector 130*b*1 is pressed. A dotted line represents the braking parameter PB in the acceleration in a case in which the level selector 130*b*2 is pressed. A single-dot dashed line represents the braking parameter PB in the acceleration in a case in which the level selector 130*b*3 is pressed. A double-dot dashed line represents the braking parameter PB in the acceleration in a case in which the level selector 130*b*4 is pressed. A gradient of the braking parameter PB, and the maximum value of the absolute value of the braking parameter PB become greater as the selected level of the braking force PWB becomes heavier.

The braking parameter PB is a coefficient of inertia friction, for example. The servomotors SM7*a*, SM7*b* and SM7*c* are controlled so as to apply the braking force PWB corresponding to an inertial friction force obtained by multiplying the coefficient of inertia friction by an acceleration.

The operation controller 340 is configured to acquire the operation velocity V of the operation unit 110 in the Cartesian coordinate system CA based on at least one of detection results of rotation angles of the encoders EN7*a*, EN7*b*, EN7*c*, EN7*d*, EN7*e*, EN7*f* and EN7*g*. The operation controller 340 is configured to determine the braking parameter PB in accordance with the acquired operation velocity V of the operation unit 110 and the selected level of the braking force PWB. For example, in the deceleration of the operation of the operation unit 110, the operation controller 340 can determine the braking parameter PB by using information such as a table that maps the operation velocity V of the operation unit 110, the level of the force PWA, and the operation parameter PA correspondingly to a graph shown in FIG. 25. Also, for example, in the acceleration of the operation of the operation unit 110, the operation controller 340 can determine the braking parameter PB by using information such as a table that maps the operation velocity V of the operation unit 110, the level of the force PWA, and the operation parameter PA correspondingly to a graph shown in FIG. 26.

Figure 27:
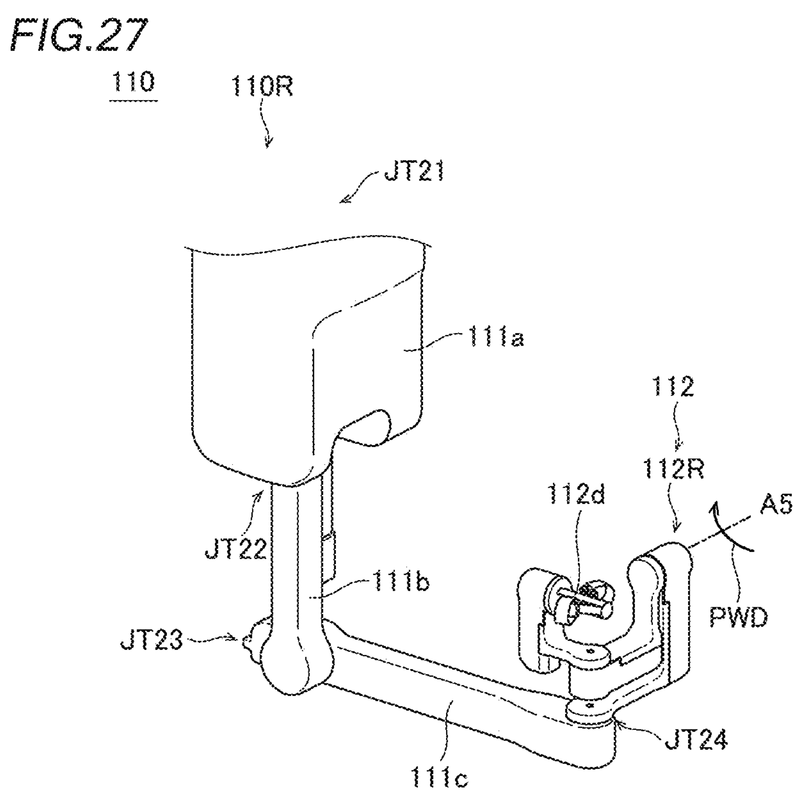
FIG. 27 is a view illustrating application of a start-from-rest assistance force in the one embodiment.

In this embodiment, as shown in FIG. 27, the operation controller 340 is configured to apply a start-from-rest assistance force PWD when the operation unit 110 starts from rest by controlling the servomotor SM7*e* of the joint JT25 that corresponds to an upward movement of the grip part 112*d* in the plurality of joints JT21, JT22, JT23, JT24, JT25, JT26 and JT27. Specifically, the operation controller 340 controls the servomotor SM7*e* so as to apply the start-from-rest assistance force PWD in a rotational direction about an axis A5 of the joint JT25. For example, the operation controller 340 controls the servomotor SM7*e* so as to increase the start-from-rest assistance force PWD as the acceleration of the operation unit 110 increases. The start-from-rest assistance force PWD refers to a force that assists the operation unit 110 for light operation of the operation unit 110 in initial movement when the operation unit 110 starts from rest and is accelerated.

Figure 28:
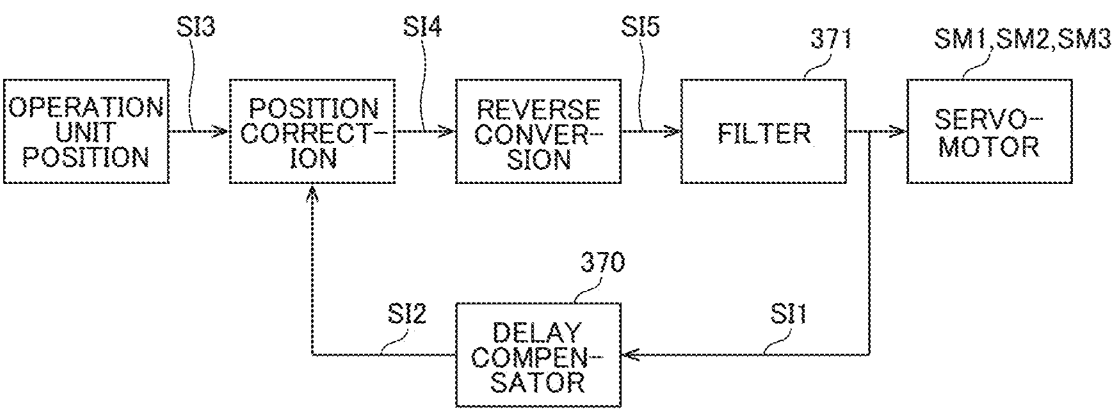
FIG. 28 is a diagram illustrating compensation of a delay in the one embodiment.

In this embodiment, as shown in FIG. 28, the robotic surgical system 500 further includes a delay compensator 370 configured to compensate for a delay between an input of the operation of the operation unit 110 and an output to the robot arm 50 in response to the input. The delay compensator 370 is a delay compensation filter serving as a Smith predictor that predicts a delay and compensates for the delay. The delay compensator 370 is configured to predict the delay based on signals SI1 between the filter 371, such as a notch filter for shake correction, and the servomotors SM1, SM2 or SM3, and to output signals SI2 to compensate the predicted delay. The delay compensator 370 includes a delay compensation model. The delay compensation model is configured to output the signals SI2 corresponding to the signals SI1 when receiving the signals SI1. The delay compensator 370 is included in the surgical robot 100.

The SI3 signals representing a position of the operation unit 110 of the remote control apparatus 200 is first input to the first controller 310 of the surgical robot 100. The first controller 310 corrects the signals SI3 based on the signals SI2 from the delay compensator 370. Accordingly, delay-compensated signals SI4 are obtained. The first controller 310 applies reverse conversion to the signal SI4 so as to obtain the position of the robot arm 50. As a result, signals SI5 of the position of the robot arm 50 to which the position of the operation unit 110 is converted is obtained. The first controller 310 outputs the signals SI5 to the filter 371. The filter 371 attenuates a frequency band corresponding to the shake. In this case, a delay occurs due to processing of the filter 371. The first controller 310 then outputs the signals SI1 obtained by processing of the filter 371 to a servomotor SM1, SM2 or SM3 and to the delay compensator 370.

Exemplary effective timing for delay compensation of the delay compensator 370 is time that a predicted velocity of the surgical instrument 1 becomes greater than the velocity of the operation unit 110. Because the surgical instrument 1 follows the operation unit 110 and delays with respect to the operation unit, the predicted speed of the surgical instrument 1 typically becomes greater than the velocity of the operation unit 110 in deceleration. If the delay is not compensated in the deceleration, the delay will cause improper stopping at a desired position of the surgical instrument 1 so that the surgical instrument 1 will pass through the desired position. The compensating for the delay can prevent the surgical instrument 1 from passing through the desired position.

Advantages of the Embodiment

In this embodiment, as described above, the operation controller 340 is configured to control the servomotors SM7*a*, SM7*b* and SM7*c* to apply a force PWA in a direction opposite to a direction of the operation of the operation unit 110 in a three-axis Cartesian coordinate system CA having three axes orthogonal to each other. Accordingly, because operation feeling of the operation unit 110 can be heavy, it is possible to prevent the operation unit from swaying due to light operation feeling of the operation unit 110 when users linearly operate the operation unit 110. Consequently, it is possible to improve stability of operation of the operation unit 110 when users linearly operate the operation unit.

Although it can be conceived that the servomotors SM7*a*, SM7*b* and SM7*c* are controlled not in the Cartesian coordinate system CA but are individually controlled to make operation feeling of the operation unit 110 heavy, forces of the servomotors SM7*a*, SM7*b* and SM7*c* become imbalanced in some cases so that the operation unit 110 will sway when users linearly operate the operation unit. Contrary to this, because the operation controller is configured to control at least one of the servomotors SM7*a*, SM7*b*, and SM7*c* so as to apply the force PWA in a direction opposite to a direction of the operation of the operation unit 110 in the Cartesian coordinate system CA, it is possible to prevent such an imbalance of between the forces of the servomotors SM7*a*, SM7*b* and SM7*c*. Also, for this reason, because the operation unit 110 can be prevented from swaying when users linearly operate the operation unit, it is possible to improve stability of operation of the operation unit 110 when users linearly operate the operation unit.

In this embodiment, as described above, the robotic surgical system 500 includes an acceptor 130*a* configured to accept a force-changing operation to change a level of the force PWA of the operator, and the operation controller 340 is configured to change the level of the force PWA in accordance with the force-changing operation for changing the level of the force PWA accepted by the acceptor 130*a*. Accordingly, because the level of the force PWA can be changed in accordance with the operator, an appropriate force PWA can be applied to the operator in accordance with a desired force for the operator. Consequently, it is possible to effectively prevent the operation unit 110 from swaying when the user linearly operates the operation unit.

In this embodiment, as described above, the operation controller 340 is configured to determine an operation parameter PA of the servomotors SM7*a*, SM7*b* and SM7*c* based on an operation velocity V of the operation unit 110, and to control the servomotor SM7*a*, controls SM7*b* and SM7*c* so as to apply the force PWA based on the operation parameter PA determined. Accordingly, it is possible to appropriately apply the force PWA to the operation unit based on the operation parameter PA determined in accordance with the operation velocity V of the operation unit 110.

In this embodiment, as described above, the operation controller 340 is configured to increase, if an absolute value of the operation velocity V of the operation unit 110 is not greater than a first threshold value TH1, the absolute value of the operation parameter PA as the absolute value of the operation velocity V of the operation unit 110 increases, and to fix the absolute value of the operation parameter PA at a maximum value if the absolute value of the operation velocity V of the operation unit 110 is greater than the first threshold value TH1. Accordingly, because, if an absolute value of the operation velocity V of the operation unit 110 is not greater than a first threshold value TH1, the absolute value of the operation parameter PA is increase as the absolute value of the operation velocity V of the operation unit 110 increases, it is possible to prevent that the operator feels wrongness caused by a directional change of the force PWA in the operation velocity V close to zero. Also, because, if the absolute value of the operation velocity V of the operation unit 110 is greater than the first threshold value TH1, the absolute value of the operation parameter PA is fixed at the maximum value, it is possible to effectively prevent the operation unit 110 from swaying when the user linearly operates the operation unit.

In this embodiment, as described above, the operation controller 340 is configured to control the servomotors SM7*a*, SM7*b* and SM7*c* so as to apply the braking force PWB in the Cartesian coordinate system CA in deceleration and/or acceleration of the operation of the operation unit 110. Accordingly, because the PWB braking force is applied in deceleration of the operation of the operation unit 110, it is possible to prevent that inertia causes the operation unit 110 to overshoot a target point when the operation unit 110 is rapidly stopped. Also, because the PWB braking force is applied in acceleration of the operation of by the operation unit 110, it is possible to prevent movement of the operation unit 110 in response to a rapid stop of the operation unit 110, or the like. Consequently, it is possible to stop the operation unit 110 at an appropriate position.

In this embodiment, as described above, the robotic surgical system 500 includes an acceptor 130*a* configured to accept a force-changing operation to change a level of the braking force PWB of the operator, and the operation controller 340 is configured to change the level of the braking force PWB in accordance with the force-changing operation for changing the level of the braking force PWB accepted by the acceptor 130*a*. Accordingly, because the level of the braking force PWB can be changed in accordance with the operator, an appropriate braking force PWB can be applied to the operator in accordance with a desired force for the operator. Consequently, it is possible to effectively stop the operation unit 110 at an appropriate position.

In this embodiment, as described above, the operation controller 340 is configured to determine a braking parameter PB of the servomotors SM7*a*, SM7*b* and SM7*c* in deceleration and/or acceleration of the operation of the operation unit 110, and to control the servomotor SM7*a*, controls SM7*b* and SM7*c* so as to apply the braking force PWB based on the braking parameter PB determined. Accordingly, it is possible to appropriately apply the braking force PWB to the operation unit based on the operation parameter PB.

In this embodiment, as described above, the operation controller 340 is configured to fix the braking parameter PB at a constant value in the deceleration of the operation of the operation unit 110. Accordingly, because the PWB braking force fixed can applied in deceleration of the operation of the operation unit 110, it is possible to easily prevent that inertia of the operation unit 110 causes the operation unit 110 to overshoot a target point when the operation unit 110 is rapidly stopped.

In this embodiment, as described above, the operation controller 340 is configured, in the acceleration of the operation of the operation unit 110, to fix the braking parameter PB at a maximum value if the absolute value of the operation velocity V of the operation unit 110 is not greater than a second threshold value TH2, to reduce the braking parameter PB as the operation velocity V of the operation unit 110 increases if the absolute value of the operation velocity V of the operation unit 110 is greater than the second threshold value TH2 and not greater than a third threshold value TH3, and to set the braking parameter PB zero if the absolute value of the operation velocity V of the operation unit 110 is greater than the third threshold value TH3. Accordingly, because, if an absolute value of the operation velocity V of the operation unit 110 is not greater than a second threshold value TH2, the braking parameter PB is fixed at the maximum value, it is possible to prevent movement of the operation unit 110 in response to a rapid stop of the operation unit 110, or the like in a low speed range. Also, because, if the absolute value of the operation velocity V of the operation unit 110 is greater than the second threshold value TH2 and not greater than a third threshold value TH3, the braking parameter PB is reduced as the operation velocity V of the operation unit 110 increases so that the operation parameter PB can be smoothly varied, it is possible to prevent that the operator feels wrongness caused by the variation of the operation parameter PB. Also, because, if the absolute value of the operation velocity V of the operation unit 110 is greater than the third threshold value TH3, the braking parameter PB is set zero, the user can feel light when operating the operation unit 110 in a high speed range.

In this embodiment, as described above, the operation unit 110 includes a plurality of joints JT21, JT22, JT23, JT24, JT25, JT26 and JT27; each of the servomotors is provided to correspond one of the plurality of joints JT21, JT22, JT23, JT24, JT25, JT26 and JT27; and the operation controller 340 is configured to apply the force PWA by controlling the servomotors SM77*a*, SM77*b* and SM77*c*, which are provided to three JT21, JT22 and JT23 that are connected closer to a proximal end of the operation unit 110 in the plurality of joints JT21, JT22, JT23, JT24, JT25, JT26 and JT27. Accordingly, the servomotors SM7*a*, SM7*b* and SM7*c* corresponding to joints JT21, JT22 and JT23, which are configured to move the surgical instrument 1, can apply the force PWA it is possible to improve stability of operation of the operation unit 110 when the surgical instrument 1 is moved by the robot arm 50.

In this embodiment, as described above, the operation unit 110 includes the plurality of joint (JT21, JT22, JT23, JT24, JT25, JT26, JT27, and a grip part 112*d* configured to be gripped by the operator; each of the servomotors is provided to correspond one of the plurality of joints JT21, JT22, JT23, JT24, JT25, JT26 and JT27; and the operation controller 340 is configured to apply a start-from-rest assistance force PWD when the operation unit 110 starts from rest by controlling the servomotor SM7*e* of the joint JT25 that corresponds to an upward movement of the grip part 112*d* in the plurality of joints JT21, JT22, JT23, JT24, JT25, JT26 and JT27. Accordingly, because, when the operator moves the grip part 112*d* upward, the start-from-rest assistance force PWD can be applied to the operation unit, the operator can easily move the grip part 112*d* upward.

In this embodiment, as described above, the robotic surgical system 500 includes a delay compensator 370 configured to compensate for a delay between an input of the operation of the operation unit 110 and an output to the robot arm 50 in response to the input. Accordingly, because overshooting of the surgical instrument 1, which is a subject to be operated by using the operation unit 110, caused by the delay can be prevented, the user can stop the surgical instrument 1 at an appropriate position.

Modified Embodiments

Note that the embodiment disclosed this time must be considered as illustrative in all points and not restrictive. The scope of the present invention is not shown by the above description of the embodiments but by the scope of claims for patent, and all modifications or modified examples within the meaning and scope equivalent to the scope of claims for patent are further included.

While the example in which if an absolute value of the operation velocity V of the operation unit 110 is not greater than a first threshold value TH1, the absolute value of the operation parameter PA is increased as the absolute value of the operation velocity V of the operation unit 110 increases has been shown in the aforementioned embodiment, the present disclosure is not limited to this. For example, alternatively, the absolute value of the operation parameter PA can be constant without using the first threshold value TH1.

While the example in which if the absolute value of the operation velocity V of the operation unit 110 becomes greater than the absolute value of the first threshold value TH1, the absolute value of the operation parameter PA is fixed at the maximum value has been shown in the aforementioned embodiment, the present disclosure is not limited to this. For example, alternatively, the absolute value of the operation parameter PA can be increased as the absolute value of the operation velocity V of the operation unit 110 increases in all the range without using the first threshold value TH1.

While the example in which the braking parameter PB is fixed in the deceleration of the operation of the operation unit 110 has been shown in the aforementioned embodiment, the present disclosure is not limited to this. For example, alternatively, the absolute value of the braking parameter PB can be increased as the absolute value of the operation velocity V of the operation unit 110 increases in the deceleration of the operation of the operation unit 110. Also, a threshold can be used similar to the operation parameter PA. That is, if the absolute value of the operation velocity V of the operation unit 110 is not greater than the threshold value, the absolute value of the braking parameter PB is increased as the absolute value of the operation velocity V of the operation unit 110 increases, and if the absolute value of the operation velocity V of the operation unit 110 is greater than the threshold value, the absolute value of the braking parameter PB can be fixed.

While the example in which if the absolute value of the operation velocity V of the operation unit 110 is not greater than the absolute value of the second threshold value TH2, the absolute value of the braking parameter PB is fixed at the maximum value in the acceleration of the operation of the operation unit 110. For example, alternatively, if the absolute value of the operation velocity V of the operation unit 110 is not greater than the absolute value of the second threshold value TH2, the absolute value of the braking parameter PB can be increased as the absolute value of the operation velocity V of the operation unit 110 increases in the acceleration of the operation of the operation unit 110.

While the example in which if the absolute value of the operation velocity V of the operation unit 110 becomes greater than the absolute value of the third threshold value TH3, the braking parameter PB is fixed at zero in the acceleration of the operation of the operation unit 110 has been shown in the aforementioned embodiment, the present disclosure is not limited to this. For example, alternatively, if the absolute value of the operation velocity V of the operation unit 110 becomes greater than the absolute value of the third threshold value TH3, the braking parameter PB is fixed at a value other than zero in the acceleration of the operation of the operation unit 110.

While the example in which the acceptor 130*a* is provided to the remote control apparatus 200 has been shown in the aforementioned embodiment, the present disclosure is not limited to this. For example, alternatively, the acceptor 130*a* can be located in a place other than the remote control apparatus 200.

While the example in which the acceptor 130*a* is constructed of a touch panel has been shown in the aforementioned embodiment, the present disclosure is not limited to this. For example, alternatively, the acceptor 130*a* can include a keyboard, a trackball, a mouse, a lever, a dial, a joystick, a foot switch, a press button switch, and/or a combination of them.

While the example in which the acceptor 130*a* is configured to accept a force-changing operation to change a level of the force PWA of the operator, and a force-changing operation to change a level of the braking force PWB of the operator has been shown in the aforementioned embodiment, the present disclosure is not limited to this. For example, alternatively, a first acceptor configured to accept a force-changing operation to change a level of the force PWA of the operator, and a second acceptor configured to accept a force-changing operation to change a level of the braking force PWB of the operator can be separately provided.

While the example in which the acceptor 130*a* is provided has been shown in the aforementioned embodiment, the present disclosure is not limited to this. For example, the acceptor 130*a* is not necessarily provided.

While the example in which the servomotors SM7*a*, SM7*b* and SM7*c* are controlled so as to apply the force PWA has been shown in the aforementioned embodiment, the present disclosure is not limited to this. In the present disclosure, alternatively, any of the servomotor can be controlled as long as it can appropriately apply the force PWA.

While the example in which the operation controller 340 is configured to control the force PWA and the braking force PWB applied to the operation unit has been shown in the aforementioned embodiment, the present disclosure is not limited to this. In the present disclosure, alternatively, a component other than the operation controller 340 can be configured to control the force PWA and the braking force PWB applied to the operation unit While the example in which a start-from-rest assistance force PWD is applied to the operation unit when the operation unit 110 starts from rest by controlling the servomotor SM7*e* of the joint JT25 that corresponds to an upward movement of the grip part 112*d* has been shown in the aforementioned embodiment, the present disclosure is not limited to this. In the present disclosure, the start-from-rest assistance force PWD is not necessarily applied to the operation unit when the operation unit 110 starts from rest by controlling the servomotor SM7*e* of the joint JT25 that corresponds to an upward movement of the grip part 112*d*

While the example in which the delay compensator 370 is provided has been shown in the aforementioned embodiment, the present disclosure is not limited to this. For example, the delay compensator 370 is not necessarily provided.

While the example in which four robot arms 50 are provided has been shown in the aforementioned embodiment, the present disclosure is not limited to this. In the present disclosure, alternatively, any number of robot arms 50 can be provided as long as at least one robot arm is provided.

While the example in which the arms 51 and the positioner 30 are constructed of a 7-axis multi-joint robot has been shown in the aforementioned embodiment, the present disclosure is not limited to this. For example, the arms 51 and the positioner 30 are constructed of a multi-joint robot having an axis configuration other than the 7-axis multi-joint robot. The multi-joint robot having an axis configuration other than the 7-axis multi-joint robot can be a 6-axis or 8-axis multi-joint robot, for example.

While the example in which the surgical robot 100 includes the medical cart 10, the positioner 30 and the arm base 40 has been shown in the aforementioned embodiment, the present disclosure is not limited to this. The medical cart 10, the positioner 30 and the arm base 40 are not necessarily provides, and the surgical robot 100 may include only the robot arms 50, for example.

Functions of elements disclosed in this specification can be realized by a circuit or processing circuit including a general purpose processor, a dedicated processor, an Integrated circuit, ASIC (Application Specific Integrated Circuits), a conventional circuit and/or combination of them configured or programmed to realize the functions disclosed. Because processors include transistors and other circuits, they are considered as a processing circuit or a circuit. In the present disclosure, circuits, units or means are hardware for realizing the functions stated above, or hardware programmed to realize the functions stated above. The hardware can be hardware disclosed in this specification, or can be other known hardware programed or configured to realize the functions stated above. In the case in which the hardware is a processor that can be considered as one type of circuits, the circuit, means or unit is a combination of hardware and software, and the software is used for configuration of the hardware and/or the processor.

Modes

The aforementioned exemplary embodiment will be understood as concrete examples of the following modes by those skilled in the art.

(Mode Item 1)

A robotic surgical system according to mode item 1 includes a surgical apparatus including a robot arm configured to support a medical instrument; an operation apparatus including an operation unit that is configured to accept operation of an operator and includes a driver(s) configured to assist the operation of the operator, and being configured to operate the surgical apparatus; and a controller configured to control the driver(s) to apply a force in a direction opposite to a direction of the operation of the operation unit in a three-axis Cartesian coordinate system having three axes orthogonal to each other.

(Mode Item 2)

In the robotic surgical system according to mode item 1, a first acceptor configured to accept a force-changing operation to change a level of the force of the operator is further provided, wherein the controller is configured to change the level of the force in accordance with the force-changing operation accepted by the first acceptor.

(Mode Item 3)

In the robotic surgical system according to mode item 1 or 2, the controller is configured to determine an operation parameter of the driver(s) based on an operation velocity of the operation unit, and to control the driver(s) so as to apply the force based on the operation parameter determined.

(Mode Item 4)

In the robotic surgical system according to mode item 3, the controller is configured to increase, if an absolute value of the operation velocity of the operation unit is not greater than a first threshold value, an absolute value of the operation parameter as the absolute value of the operation velocity of the operation unit increases, and to fix the absolute value of the operation parameter at a maximum value if the absolute value of the operation velocity of the operation unit is greater than the first threshold value.

(Mode Item 5)

In the robotic surgical system according to any of mode items 1 to 4, the controller is configured to control the driver(s) so as to apply a braking force in the Cartesian coordinate system in deceleration and/or acceleration of the operation of the operation unit.

(Mode Item 6)

In the robotic surgical system according to mode item 5, a second acceptor configured to accept a braking-force-changing operation to change a level of the braking force of the operator is further provided, wherein the controller is configured to change the level of the braking force in accordance with the braking-force-changing operation accepted by the second acceptor.

(Mode Item 7)

In the robotic surgical system according to mode item 5 or 6, the controller is configured to determine, in the deceleration and/or the acceleration of the operation of the operation unit, a braking parameter of the driver(s), and to control the driver(s) so as to apply the braking force based on the braking parameter determined.

(Mode Item 8)

In the robotic surgical system according to mode item 7, the controller is configured to fix the braking parameter at a constant value in the deceleration of the operation of the operation unit.

(Mode Item 9)

In the robotic surgical system according to mode item 7 or 8, the controller is configured, in the acceleration of the operation of the operation unit, to fix the braking parameter at a maximum value if an/the absolute value of the operation velocity of the operation unit is not greater than a second threshold value, to reduce the braking parameter as the operation velocity of the operation unit increases if the absolute value of the operation velocity of the operation unit is greater than the second threshold value and not greater than a third threshold value, and to set the braking parameter zero if the absolute value of the operation velocity of the operation unit is greater than the third threshold value.

(Mode Item 10)

In the robotic surgical system according to any of mode items 1 to 9, the operation unit includes a plurality of joints; each of the drivers is provided to correspond one of the plurality of joints; and the controller is configured to apply the force by controlling the drivers that are provided to three of the joints that are connected closer to a proximal end of the operation unit in the plurality of joints.

(Mode Item 11)

In the robotic surgical system according to any of mode items 1 to 10, the operation unit includes a/the plurality of joints, and a grip part configured to be gripped by the operator; each of the drivers is provided to correspond one of the plurality of joints; and the controller is configured to apply a start-from-rest assistance force when the operation unit starts from rest by controlling the driver of the rotation shaft that corresponds to an upward movement of the grip part in the plurality of joints.

(Mode Item 12)

In the robotic surgical system according to any of mode items 1 to 11, a delay compensator configured to compensate for a delay between an input of the operation of the operation unit and an output to the robot arm in response to the input is further provided.

(Mode Item 13)

An operation apparatus according to mode item 13 is an operation apparatus for operating a surgical apparatus including a robot arm configured to support a medical instrument, the operation apparatus including an operation unit that is configured to accept operation of an operator and includes a driver(s) configured to assist the operation of the operator; and a controller configured to control the driver(s) to apply a force in a direction opposite to a direction of the operation of the operation unit in a three-axis Cartesian coordinate system having three axes orthogonal to each other.

(Mode Item 14)

A method according to mode item 14 is a method for controlling a robotic surgical system including a surgical apparatus including a robotic arm configured to support a medical instrument, and an operation apparatus including an operation unit that is configured to accept operation of an operator and includes a driver(s) configured to assist the operation of the operator, and being configured to operate the surgical apparatus, the method including accepting the operation of the operation unit; and controlling the driver(s) to apply a force in a direction opposite to a direction of the operation of the operation unit in a three-axis Cartesian coordinate system having three axes orthogonal to each other.

What is claimed is:

1. An operation apparatus for operating a surgical apparatus including a robot arm configured to support a medical instrument, the operation apparatus comprising:

an operation unit comprising an input device and a handle configured to accept operation of an operator and includes one or more drivers configured to assist the operation of the operator; and a controller configured to perform operations further comprising operations to:

control the one or more drivers to apply a force in a direction opposite to a direction of the operation of the operation unit in a three-axis Cartesian coordinate system having three axes orthogonal to each other, and control the one or more drivers so as to apply a braking force in the Cartesian coordinate system in one or more of: a deceleration and an acceleration of the operation of the operation unit.

2. The operation apparatus according to claim 1, further comprising a second acceptor configured to accept a braking-force-changing operation to change a level of the braking force of the operator, wherein the controller is configured to perform operations further comprising operations to change the level of the braking force in accordance with the braking-force-changing operation accepted by the second acceptor.

3. The operation apparatus according to claim 1, wherein the controller is configured to perform operations further comprising operations to determine, in the one or more of the deceleration and the acceleration of the operation of the operation unit, a braking parameter of the one or more drivers, and to control the one or more drivers so as to apply the braking force based on the braking parameter determined.

4. The operation apparatus according to claim 1, further comprising a delay compensator comprising a filter configured to compensate for a delay between an input of the operation of the operation unit and an output to the robot arm in response to the input.

5. A robotic surgical system, comprising:

a surgical apparatus including a robot arm configured to support a medical instrument;

an operation apparatus including an operation unit comprising an input device and a handle configured to accept operation of an operator and includes one or more drivers configured to assist the operation of the operator, and being configured to operate the surgical apparatus; and a controller configured to perform operations comprising operations to:

control the one or more drivers to apply a force in a direction opposite to a direction of the operation of the operation unit in a three-axis Cartesian coordinate system having three axes orthogonal to each other; and control the one or more drivers so as to apply a braking force in the Cartesian coordinate system in one of: a deceleration and an acceleration of the operation of the operation unit.

6. The robotic surgical system according to claim 5, wherein the input device further comprises a touch panel display that displays elements comprising:

a first acceptor configured to accept a force-changing operation to change a level of the force of the operator; and a second acceptor configured to accept a braking-force-changing operation to change a level of the braking force of the operator, wherein the controller is configured to perform operations further comprising operations to:

change the level of the force in accordance with the force-changing operation accepted by the first acceptor; and change the level of the braking force in accordance with the braking-force-changing operation accepted by the second acceptor.

7. The robotic surgical system according to claim 5, wherein the controller is configured to perform operations further comprising operations to determine, in the one or more of: the deceleration and the acceleration of the operation of the operation unit, a braking parameter of the one or more drivers, and to control the one or more drivers so as to apply the braking force based on the braking parameter determined.

8. The robotic surgical system according to claim 7, wherein the controller is configured to perform operations further comprising operations to fix the braking parameter at a constant value in the deceleration of the operation of the operation unit.

9. The robotic surgical system according to claim 7, wherein the controller is configured to perform operations further comprising operations, in the acceleration of the operation of the operation unit, to fix the braking parameter at a maximum value if an absolute value of the operation velocity of the operation unit is not greater than a second threshold value, to reduce the braking parameter as the operation velocity of the operation unit increases if the absolute value of the operation velocity of the operation unit is greater than the second threshold value and not greater than a third threshold value, and to set the braking parameter zero if the absolute value of the operation velocity of the operation unit is greater than the third threshold value.

10. A method for controlling a robotic surgical system including a surgical apparatus including a robot arm configured to support a medical instrument, and an operation apparatus including an operation unit comprising an input device and a handle configured to accept operation of an operator and includes one or more drivers configured to assist the operation of the operator, and being configured to operate the surgical apparatus, the method comprising:

accepting the operation of the operation unit;

controlling the one or more drivers to apply a force in a direction opposite to a direction of the operation of the operation unit in a three-axis Cartesian coordinate system having three axes orthogonal to each other;

determining an operation parameter of the one or more drivers based on an operation velocity of the operation unit, and controlling the one or more drivers so as to apply the force based on the operation parameter determined, and increasing, if an absolute value of the operation velocity of the operation unit is not greater than a first threshold value, an absolute value of the operation parameter as the absolute value of the operation velocity of the operation unit increases, and fixing the absolute value of the operation parameter at a maximum value if the absolute value of the operation velocity of the operation unit is greater than the first threshold value.

11. A robotic surgical system, comprising:

a surgical apparatus including a robot arm configured to support a medical instrument;

an operation apparatus including an operation unit comprising an input device and a handle configured to accept operation of an operator and includes one or more drivers configured to assist the operation of the operator, and being configured to operate the surgical apparatus; and a controller configured to perform operations comprising operations to:

control the one or more drivers to apply a force in a direction opposite to a direction of the operation of the operation unit in a three-axis Cartesian coordinate system having three axes orthogonal to each other;

determine an operation parameter of the one or more drivers based on an operation velocity of the operation unit, and to control the one or more drivers so as to apply the force based on the operation parameter determined; and increase, if an absolute value of the operation velocity of the operation unit is not greater than a first threshold value, an absolute value of the operation parameter as the absolute value of the operation velocity of the operation unit increases, and fix the absolute value of the operation parameter at a maximum value if the absolute value of the operation velocity of the operation unit is greater than the first threshold value.

12. The robotic surgical system according to claim 11, wherein the input device further comprises a touch panel display that displays elements comprising a first acceptor configured to accept a force-changing operation to change a level of the force of the operator, wherein the controller is configured to perform operations comprising operations to change the level of the force in accordance with the force-changing operation accepted by the first acceptor.

13. A robotic surgical system comprising:

a surgical apparatus including a robot arm configured to support a medical instrument;

an operation apparatus including an operation unit comprising an input device and a handle configured to accept operation of an operator and includes one or more drivers configured to assist the operation of the operator, and being configured to operate the surgical apparatus; and a controller configured to perform operations comprising operations to control the one or more drivers to apply a force in a direction opposite to a direction of the operation of the operation unit in a three-axis Cartesian coordinate system having three axes orthogonal to each other, wherein the operation unit includes a plurality of joints;

each of the one or more drivers is provided to correspond one of the plurality of joints; and the controller is configured to perform operations further comprising operations to apply the force by controlling the one or more drivers that are provided to three of the joints that are connected closer to a proximal end of the operation unit in the plurality of joints.

14. The robotic surgical system according to claim 11, wherein the operation unit includes a plurality of joints, and a grip part configured to be gripped by the operator;

each of the one or more drivers is provided to correspond one of the plurality of joints; and the controller is configured to perform operations further comprising operations to apply a start-from-rest assistance force when the operation unit starts from rest by controlling the driver of the rotation shaft that corresponds to an upward movement of the grip part in the plurality of joints.

15. The robotic surgical system according to claim 11, further comprising a delay compensator comprising a filter configured to compensate for a delay between an input of the operation of the operation unit and an output to the robot arm in response to the input.

16. The operation apparatus according to claim 1, further comprising a first acceptor configured to accept a force-changing operation to change a level of the force of the operator, wherein the controller is configured to perform operations further comprising operations to change the level of the force in accordance with the force-changing operation accepted by the first acceptor.

17. The operation apparatus according to claim 1, wherein the controller is configured to perform operations further comprising operations to determine an operation parameter of the one or more drivers based on an operation velocity of the operation unit, and to control the one or more drivers so as to apply the force based on the operation parameter determined.

* * * * *